(12) United States Patent
Miyamoto et al.

(10) Patent No.: US 11,274,339 B2
(45) Date of Patent: Mar. 15, 2022

(54) PRIMER SET, KIT AND METHOD FOR DETECTING TWO OR MORE TARGET NUCLEIC ACIDS

(71) Applicant: KANEKA CORPORATION, Osaka (JP)

(72) Inventors: Shigehiko Miyamoto, Hyogo (JP); Takashi Nishizono, Hyogo (JP)

(73) Assignee: KANEKA CORPORATION, Osaka (JP)

( * ) Notice: Subject to any disclaimer, the term of this patent is extended or adjusted under 35 U.S.C. 154(b) by 278 days.

(21) Appl. No.: 16/238,309

(22) Filed: Jan. 2, 2019

(65) Prior Publication Data
US 2019/0119727 A1    Apr. 25, 2019

Related U.S. Application Data

(63) Continuation of application No. PCT/JP2017/022314, filed on Jun. 16, 2017.

(30) Foreign Application Priority Data

Jul. 1, 2016    (JP) .............................. JP2016-132066

(51) Int. Cl.
| | |
|---|---|
| C12Q 1/686 | (2018.01) |
| C12N 15/09 | (2006.01) |
| C12Q 1/6806 | (2018.01) |
| C12Q 1/6834 | (2018.01) |
| C12Q 1/6853 | (2018.01) |
| C12Q 1/6876 | (2018.01) |
| C12Q 1/68 | (2018.01) |

(52) U.S. Cl.
CPC ............ *C12Q 1/686* (2013.01); *C12N 15/09* (2013.01); *C12Q 1/68* (2013.01); *C12Q 1/6806* (2013.01); *C12Q 1/6834* (2013.01); *C12Q 1/6853* (2013.01); *C12Q 1/6876* (2013.01); *C12Q 2600/16* (2013.01)

(58) Field of Classification Search
CPC .............................. C12Q 1/686; C12N 15/09
See application file for complete search history.

(56) References Cited

U.S. PATENT DOCUMENTS

| | | | | |
|---|---|---|---|---|
| 5,462,854 A | * | 10/1995 | Coassin ................. | C07H 21/00 435/6.1 |
| 6,054,274 A | * | 4/2000 | Sampson ............... | C12Q 1/682 435/6.14 |
| 8,460,866 B2 | | 6/2013 | Van Eijk et al. | |
| 2014/0065725 A1 | | 3/2014 | Takahashi et al. | |

FOREIGN PATENT DOCUMENTS

| | | |
|---|---|---|
| JP | 2009-165371 A | 7/2009 |
| JP | 2009-268360 A | 11/2009 |
| JP | 2016-73312 A | 5/2016 |

OTHER PUBLICATIONS

Luo, Simultaneous splicing of multiple DNA fragments in one PCR reaction, Biological Procedures Online, 15:9, 1-9, 2013. (Year: 2013).*
International Search Report issued in International Application No. PCT/JP2017/022314, dated Sep. 19, 2017 (2 pages).
Written Opinion issued in International Application No. No. PCT/JP2017/022314, dated Sep. 19, 2017 (7 pages).
Partial Supplementary European Search Report issued in corresponding EP Application No. 17819910.5, dated Jan. 16, 2020 (12 pages).

* cited by examiner

*Primary Examiner* — Samuel C Woolwine
*Assistant Examiner* — Carolyn L Greene
(74) *Attorney, Agent, or Firm* — Osha Bergman Watanabe & Burton LLP

(57) ABSTRACT

A primer set includes a terminal primer A including, in its 3'-terminal part, a nucleotide sequence that hybridizes to a 3'-terminal part of a complementary sequence of a first target nucleic acid sequence, a k-th double-headed primer including two polynucleotides linked at their 5' terminal sides, wherein one of the two polynucleotides includes, in its 3'-terminal part, a nucleotide sequence that hybridizes to a 3'-terminal part of a nucleotide sequence of a k-th target nucleic acid, and the other polynucleotide includes, in its 3'-terminal part, a nucleotide sequence that hybridizes to a 3'-terminal part of a complementary sequence of a (k+1)th target nucleic acid, and a terminal primer B including, in its 3'-terminal part, a nucleotide sequence that hybridizes to a 3'-terminal part of a nucleotide sequence of a N-th target nucleic acid.

10 Claims, 12 Drawing Sheets

Specification includes a Sequence Listing.

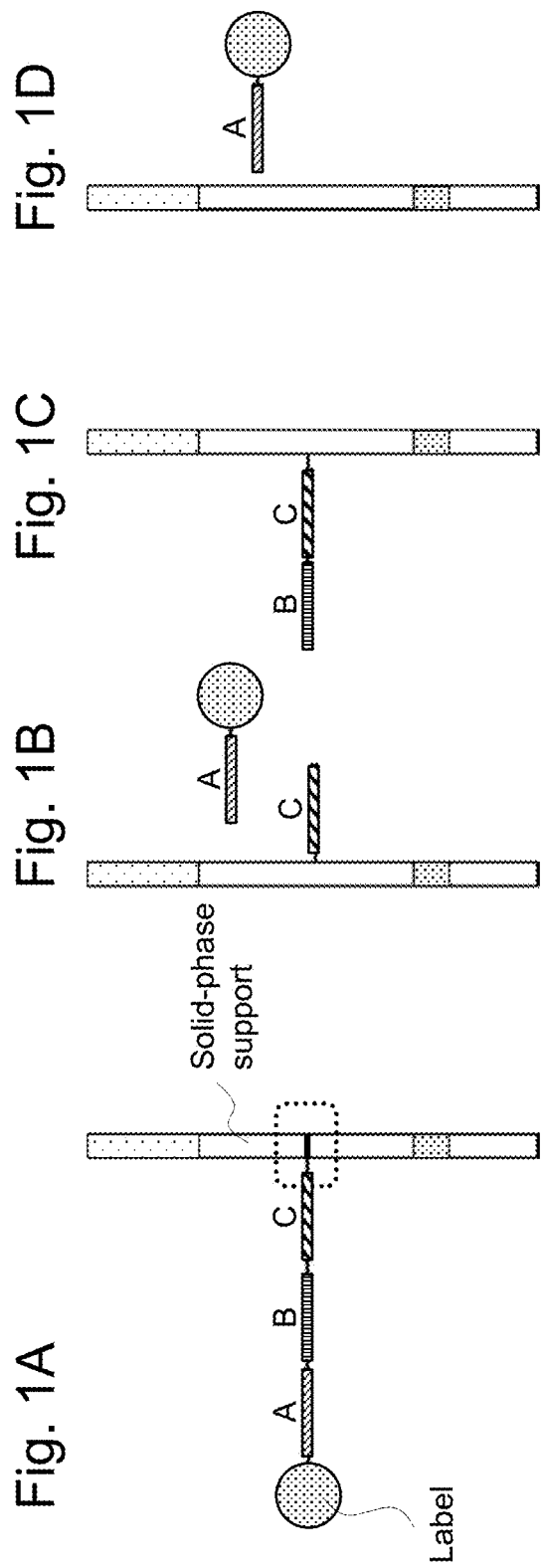

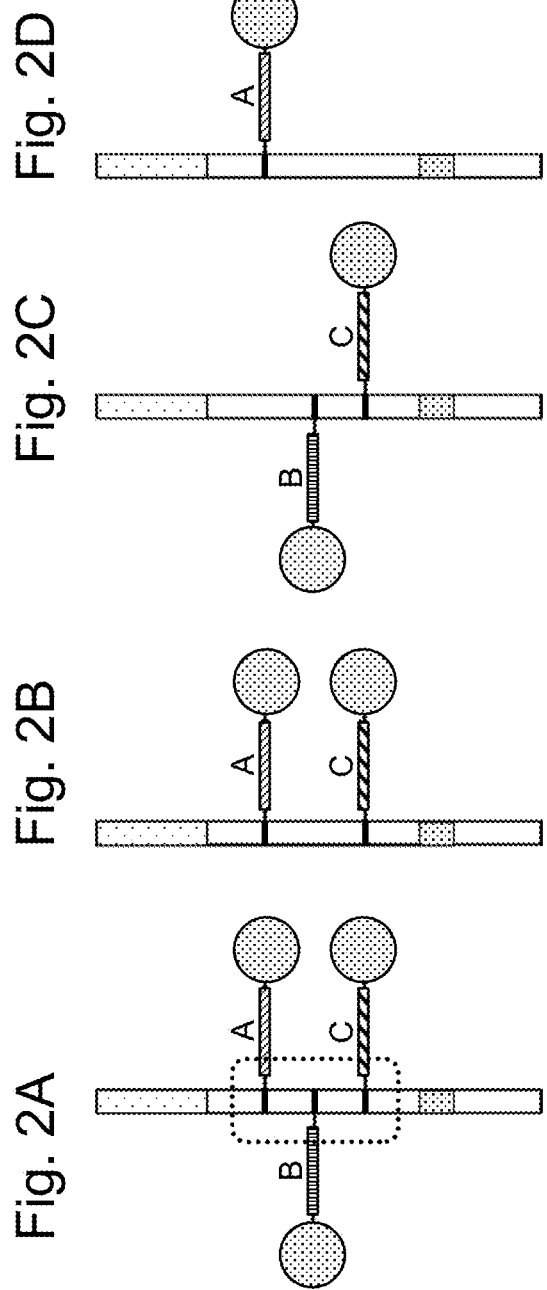

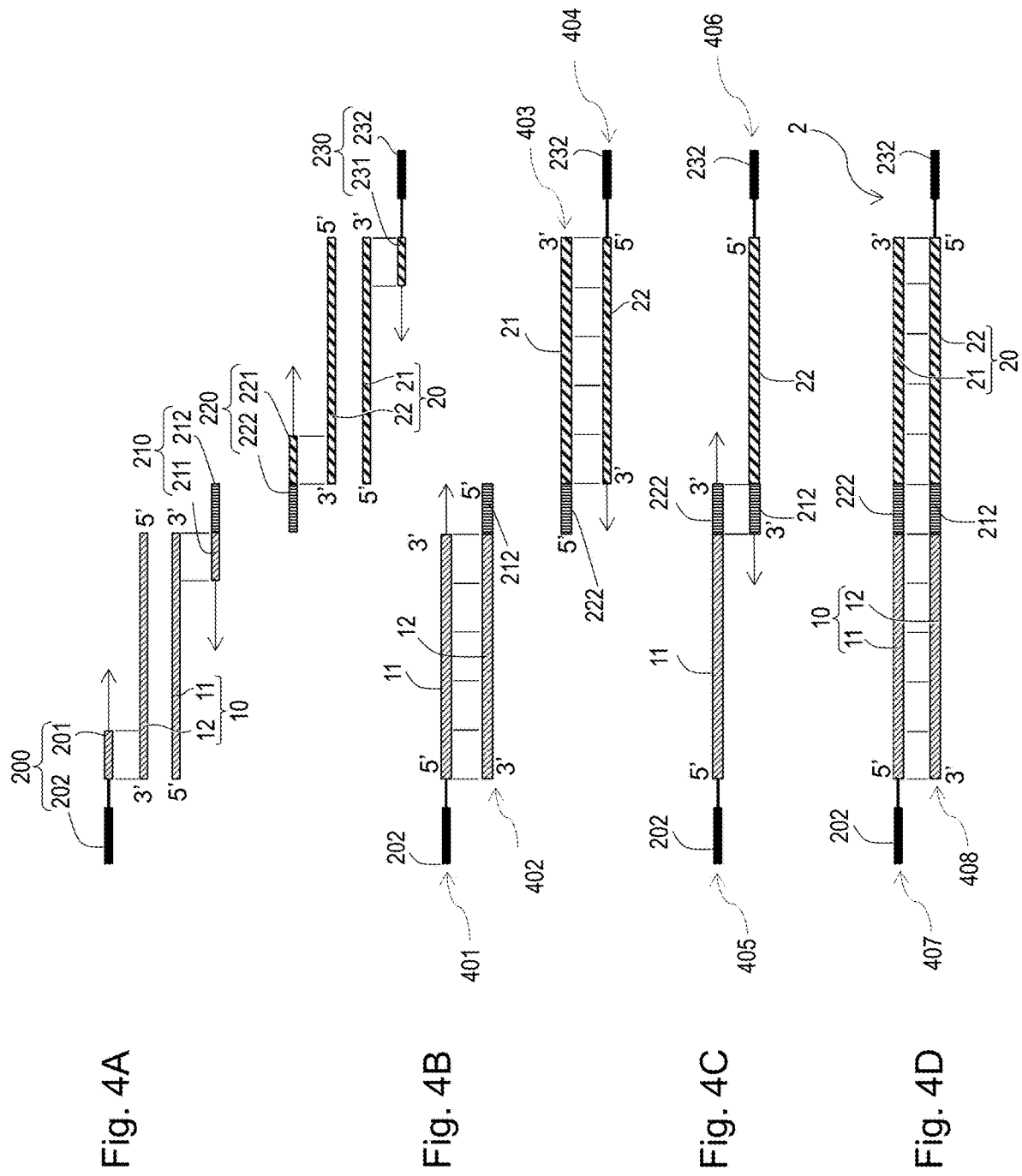

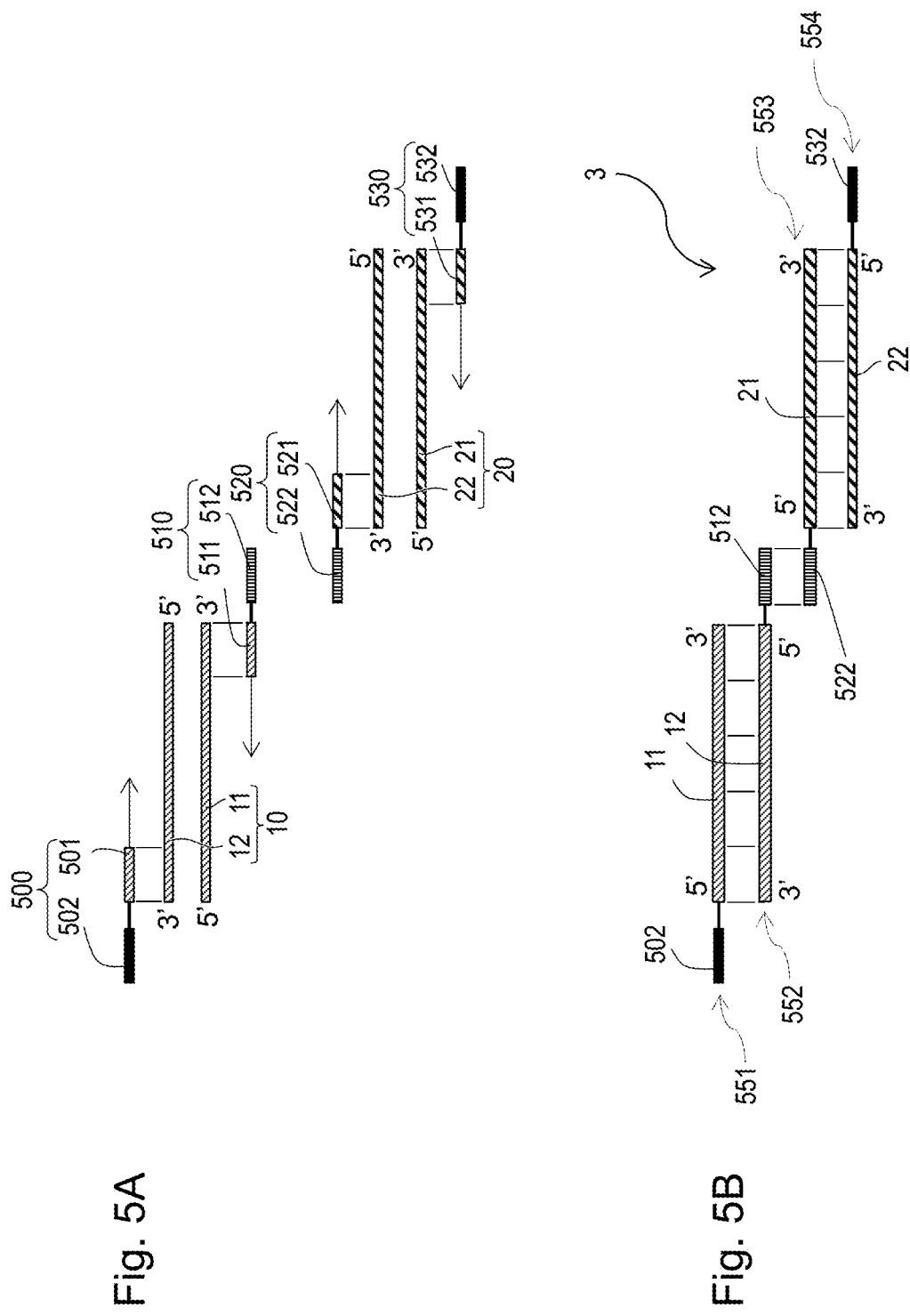

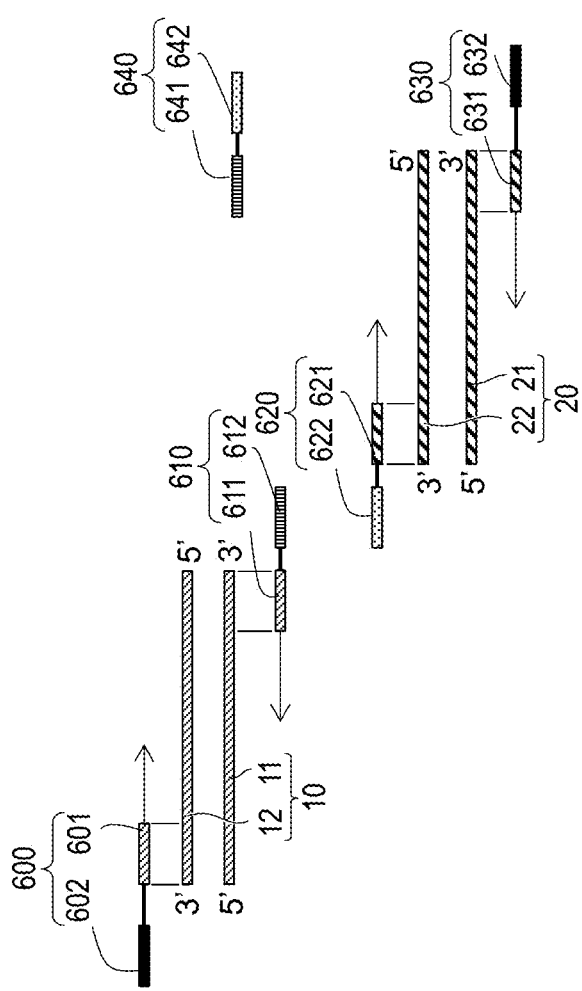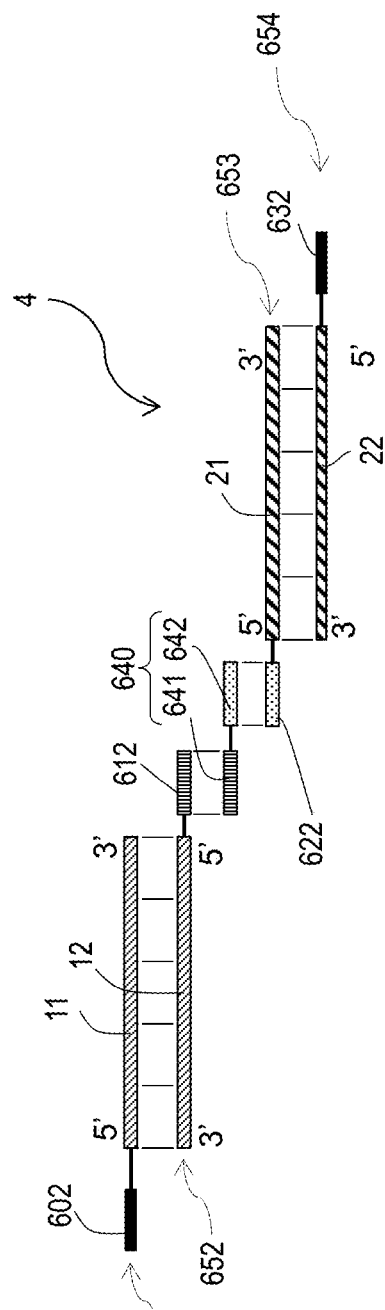

| Sample | 1 | 2 | 3 | 4 | 5 | 6 |
|---|---|---|---|---|---|---|
| Line coloring | − | − | − | − | − | + |

US 11,274,339 B2

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: TMP1F primer

<400> SEQUENCE: 1
atgcgggtat gacaaaccct                                              20

<210> SEQ ID NO 2
<211> LENGTH: 20
<212> TYPE: DNA
<213> ORGANISM: Artificial
<220> FEATURE:
<223> OTHER INFORMATION: TMP1R primer

<400> SEQUENCE: 2
ttagccccat ttggaccttt                                              20

<210> SEQ ID NO 3
```

```
<211> LENGTH: 20
<212> TYPE: DNA
<213> ORGANISM: Artificial
<220> FEATURE:
<223> OTHER INFORMATION: TMP2F primer

<400> SEQUENCE: 3
cagaccaggt aagtttctgg                                                  20

<210> SEQ ID NO 4
<211> LENGTH: 20
<212> TYPE: DNA
<213> ORGANISM: Artificial
<220> FEATURE:
<223> OTHER INFORMATION: TMP2R primer

<400> SEQUENCE: 4
cgcatatttg gtgcagaaat                                                  20

<210> SEQ ID NO 5
<211> LENGTH: 20
<212> TYPE: DNA
<213> ORGANISM: Artificial
<220> FEATURE:
<223> OTHER INFORMATION: TMP3F primer

<400> SEQUENCE: 5
tttacctcaa tggcggaacc                                                  20

<210> SEQ ID NO 6
<211> LENGTH: 20
<212> TYPE: DNA
<213> ORGANISM: Artificial
<220> FEATURE:
<223> OTHER INFORMATION: TMP3R primer

<400> SEQUENCE: 6
cccaaaagct gggttagcaa                                                  20

<210> SEQ ID NO 7
<211> LENGTH: 40
<212> TYPE: DNA
<213> ORGANISM: Artificial
<220> FEATURE:
<223> OTHER INFORMATION: TMP1F-Mem primer
<220> FEATURE:
<223> OTHER INFORMATION: The guanine nucleotide at position 20 and the
      adenine nucleotide at position 21 are linked via the divalent
      radical of formula I.

<400> SEQUENCE: 7
atgctaccgt atgcccagtg atgcgggtat gacaaaccct                            40

<210> SEQ ID NO 8
<211> LENGTH: 40
<212> TYPE: DNA
<213> ORGANISM: Artificial
<220> FEATURE:
<223> OTHER INFORMATION: TMP3F-Au primer
<220> FEATURE:
<223> OTHER INFORMATION: The adenine nucleotide at position 20 and the
      thymidine nucleotide at position 21 are linked via the divalent
      radical of formula I.

<400> SEQUENCE: 8
gacaacggag acagagccaa tttacctcaa tggcggaacc                            40
```

```
<210> SEQ ID NO 9
<211> LENGTH: 20
<212> TYPE: DNA
<213> ORGANISM: Artificial
<220> FEATURE:
<223> OTHER INFORMATION: tag sequence

<400> SEQUENCE: 9
atgctaccgt atgcccagtg                                          20

<210> SEQ ID NO 10
<211> LENGTH: 20
<212> TYPE: DNA
<213> ORGANISM: Artificial
<220> FEATURE:
<223> OTHER INFORMATION: tag sequence

<400> SEQUENCE: 10
gacaacggag acagagccaa                                          20

<210> SEQ ID NO 11
<211> LENGTH: 20
<212> TYPE: DNA
<213> ORGANISM: Artificial
<220> FEATURE:
<223> OTHER INFORMATION: tag sequence

<400> SEQUENCE: 11
cactgggcat acggtagcat                                          20

<210> SEQ ID NO 12
<211> LENGTH: 20
<212> TYPE: DNA
<213> ORGANISM: Artificial
<220> FEATURE:
<223> OTHER INFORMATION: tag sequence

<400> SEQUENCE: 12
ttggctctgt ctccgttgtc                                          20
```

PRIMER SET, KIT AND METHOD FOR DETECTING TWO OR MORE TARGET NUCLEIC ACIDS

TECHNICAL FIELD

One or more embodiments of the present invention relate to a primer set for amplifying two or more target nucleic acids as one linked amplification product.

One or more embodiments of the present invention also relate to a method for detecting two or more target nucleic acids.

One or more embodiments of the present invention also relate to a kit for detecting two or more target nucleic acids.

BACKGROUND

Methods for specifically amplifying target nucleic acids are very important techniques in the field of molecular biological research, the field of clinical application such as genetic tests, and the field of testing food or environmental hygiene. One of the methods for specifically detecting an amplification product obtained by the nucleic acid amplification method is a method which involves immobilizing an amplification product containing a target nucleic acid onto a solid phase, followed by detection. This method is capable of enhancing detection specificity by specifically capturing the target nucleic acid onto the solid phase and thereby easily removing nonspecific nucleic acid sequences by washing or the like.

In this respect, the method for capturing the target nucleic acid onto the solid phase includes a method which involves introducing a single-stranded tag region to one end of an amplification product containing the target nucleic acid, immobilizing a probe consisting of a polynucleotide having a sequence complementary to the tag region onto the solid phase, and indirectly immobilizing the target nucleic acid onto the solid phase via the hybridization between the tag region and the probe.

As a method for detecting a target nucleic acid immobilized on a solid phase, Patent Literature 1 discloses a technique of further binding a labeling agent to the target nucleic acid, followed by visual detection.

CITATION LIST

Patent Literature

Patent Literature 1: JP Patent Publication (Kokai) No. 2016-73312 A (2016)

In the technical field of specifically amplifying and testing a target nucleic acid, it may be necessary not only to confirm the amplification of a single target nucleic acid but to confirm the amplification patterns of a plurality of target nucleic acids, depending on a test subject.

FIG. 2 shows one example of the case of immobilizing amplification products of a plurality of target nucleic acids onto a solid phase and analyzing the amplification products with a labeling agent as an index. For example, amplification products of so-called multiplex PCR using a nucleic acid sample containing all of target nucleic acids A, B, and C as a template are developed onto a solid-phase support and labeled. In this case, 3 moieties on the solid-phase support are labeled as shown in FIG. 2A. By contrast, the case where the nucleic acid sample contains no target nucleic acid B (FIG. 2B), the case where the nucleic acid sample contains no target nucleic acid A (FIG. 2C), and the case where the nucleic acid sample contains neither target nucleic acid B nor C (FIG. 2D) each produce distinct labeling results. However, such an analysis method using the position or number of a labeled moiety as an index may have low identification performance, for example, when a large number of target nucleic acids are to be analyzed or when individual amplification products of a plurality of target nucleic acids are difficult to separate on a solid-phase support.

Also, the identification performance may be low when a plurality of target nucleic acids are detected on the basis of the number or mobility of bands on gel electrophoresis obtained by developing amplification products of the plurality of target nucleic acids.

Accordingly, one or more embodiments of the present invention provide an improved approach for detecting two or more target nucleic acids.

SUMMARY

One or more embodiments of the present invention disclose the following aspects.

(1) A primer set for preparing a nucleic acid amplification product detectable on a solid-phase support, the primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth double-headed primer comprising two polynucleotides linked at their 5' terminal sides, wherein one of the two polynucleotides comprises, in its 3'-terminal part, a nucleotide sequence that hybridizes to a 3'-terminal part of the nucleotide sequence of a kth target nucleic acid, and the other of the two polynucleotides comprises, in its 3'-terminal part, a nucleotide sequence that hybridizes to a 3'-terminal part of a complementary sequence of the nucleotide sequence of a (k+1)th target nucleic acid; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth double-headed primer involves the case where k is 1 to the case where k is N−1, and one of the terminal primer A and the terminal primer B further comprises a labeling part which is a labeling agent or is a tag capable of binding to a labeling agent, and the other terminal primer further comprises a binding part which is a tag capable of binding to the solid-phase support.

(2) A primer set for preparing a nucleic acid amplification product detectable on a solid-phase support, the primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth reverse primer comprising a polynucleotide which comprises, in its 3'-terminal part, nucleotide sequence $A_k$ that hybridizes to a 3'-terminal part of the nucleotide sequence of a kth target nucleic acid and further comprises nucleotide sequence $B_k$ at the 5'-terminal side of the nucleotide sequence $A_k$;

a (k+1)th forward primer comprising a polynucleotide which comprises, in its 3'-terminal part, nucleotide sequence $C_{k+1}$ that hybridizes to a 3'-terminal part of a complementary sequence of the nucleotide sequence of a (k+1)th target nucleic acid and further comprises nucleotide sequence $D_{k+1}$ that hybridizes to the nucleotide sequence $B_k$ at the 5'-terminal side of the nucleotide sequence $C_{k+1}$; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth reverse primer and the (k+1)th forward primer each involve the case where k is 1 to the case where k is N−1, and one of the terminal primer A and the terminal primer B further comprises a labeling part which is a labeling agent or is a tag capable of binding to a labeling agent, and the other terminal primer further comprises a binding part which is a tag capable of binding to the solid-phase support.

(3) A primer set for preparing a nucleic acid amplification product detectable on a solid-phase support, the primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth reverse primer comprising a polynucleotide comprising, in its 3'-terminal part, nucleotide sequence $E_k$ that hybridizes to a 3'-terminal part of the nucleotide sequence of a kth target nucleic acid, and a polynucleotide which is linked at the 5'-terminal side of the polynucleotide comprising the nucleotide sequence $E_k$ and comprises nucleotide sequence $F_k$ that is not double-stranded in nucleic acid amplification reaction;

a (k+1)th forward primer comprising a polynucleotide comprising, in its 3'-terminal part, nucleotide sequence $G_{k+1}$ that hybridizes to a 3'-terminal part of a complementary sequence of the nucleotide sequence of a (k+1)th target nucleic acid, and a polynucleotide which is linked at the 5'-terminal side of the polynucleotide comprising the nucleotide sequence $G_{k+1}$ and comprises nucleotide sequence $H_{k+1}$ that is not double-stranded in nucleic acid amplification reaction, the nucleotide sequence $H_{k+1}$ that hybridizes to the nucleotide sequence $F_k$; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth reverse primer and the (k+1)th forward primer each involve the case where k is 1 to the case where k is N−1, and one of the terminal primer A and the terminal primer B further comprises a labeling part which is a labeling agent or is a tag capable of binding to a labeling agent, and the other terminal primer further comprises a binding part which is a tag capable of binding to the solid-phase support.

(4) A primer set for preparing a nucleic acid amplification product detectable on a solid-phase support, the primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth reverse primer comprising a polynucleotide comprising, in its 3'-terminal part, nucleotide sequence $I_k$ that hybridizes to a 3'-terminal part of the nucleotide sequence of a kth target nucleic acid, and a polynucleotide which is linked at the 5'-terminal side of the polynucleotide comprising the nucleotide sequence $I_k$ and comprises nucleotide sequence $J_k$ that is not double-stranded in nucleic acid amplification reaction;

a (k+1)th forward primer comprising a polynucleotide comprising, in its 3'-terminal part, nucleotide sequence $L_{k+1}$ that hybridizes to a 3'-terminal part of a complementary sequence of the nucleotide sequence of a (k+1)th target nucleic acid, and a polynucleotide which is linked at the 5'-terminal side of the nucleotide sequence $L_{k+1}$ and further comprises nucleotide sequence $M_{k+1}$ that is not double-stranded in nucleic acid amplification reaction;

a kth linking polynucleotide comprising a polynucleotide comprising a nucleotide sequence that hybridizes to the nucleotide sequence $J_k$, and a polynucleotide comprising a nucleotide sequence that hybridizes to the nucleotide sequence $M_{k+1}$; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth reverse primer, the (k+1)th forward primer and the kth linking polynucleotide each involve the case where k is 1 to the case where k is N−1, and one of the terminal primer A and the terminal primer B further comprises a labeling part which is a labeling agent or is a tag capable of binding to a labeling agent, and the other terminal primer further comprises a binding part which is a tag capable of binding to the solid-phase support.

(5) The primer set according to any of (1) to (4), wherein the binding part is a tag comprising a polynucleotide capable of binding to the solid-phase support.

(6) A method for detecting two or more target nucleic acids, the method comprising a detection step of contacting a sample for detection possibly comprising a nucleic acid for detection comprising the two or more target nucleic acids, a labeling part which is a labeling agent or is a tag capable of binding to a labeling agent, and a binding part which is a tag capable of binding to a solid-phase support, linked to each other, with a solid-phase support at least partially comprising a moiety capable of binding to the binding part, and detecting the nucleic acid for detection at the moiety of the solid-phase support with the labeling part as an index.

(7) The method according to (6), further comprising a sample-for-detection preparation step comprising performing nucleic acid amplification reaction using a nucleic acid obtained from a sample to be analyzed as a template, and a primer set according to any of (1) to (5), wherein in the detection step, a product of the nucleic acid amplification reaction obtained in the sample-for-detection preparation step is used as the sample for detection.

(8) The method according to (7), wherein the sample-for-detection preparation step comprises performing nucleic acid amplification reaction using two or more primer sets according to any of (1) to (5) and a nucleic acid obtained from a sample to be analyzed as a template, wherein the two or more primer sets are designed so as to be able to produce two or more of the nucleic acids for detection each comprising a different combination of the two or more target nucleic acids and each having the binding part capable of binding to a distinct position of the solid-phase support, and the detection step comprises contacting the sample for detection obtained in the sample-for-detection preparation step with the solid-phase support, and detecting each of the two or more nucleic acids for detection in the solid-phase support with the labeling part as an index.

(9) A kit for detecting two or more target nucleic acids in a sample to be analyzed, the kit comprising:

a primer set according to any of (1) to (5); and a solid-phase support at least partially comprising a moiety capable of binding to the binding part.

(10) The kit according to (9), wherein the solid-phase support is comprised as a nucleic acid detection device having the solid-phase support and a reaction system reception part for receiving a product of nucleic acid amplification reaction.

(11) The kit according to (9) or (10), wherein the labeling part is a tag capable of binding to a labeling agent, and the kit further comprises a labeling agent capable of binding to the tag as the labeling part.

(12) The kit according to (11), wherein the labeling agent and the solid-phase support are comprised as a nucleic acid detection device having the solid-phase support, a labeling agent retention part which retains the labeling agent, and a reaction system reception part for receiving a product of nucleic acid amplification reaction.

(13) A primer set for preparing a nucleic acid amplification product, the primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth double-headed primer comprising two polynucleotides linked at their 5' terminal sides, wherein one of the two polynucleotides comprises, in its 3'-terminal part, a nucleotide sequence that hybridizes to a 3'-terminal part of the nucleotide sequence of a kth target nucleic acid, and the other of the two polynucleotides comprises, in its 3'-terminal part, a nucleotide sequence that hybridizes to a 3'-terminal part of a complementary sequence of the nucleotide sequence of a (k+1)th target nucleic acid; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, and the kth double-headed primer involves the case where k is 1 to the case where k is N−1.

(14) A method for detecting two or more target nucleic acids, the method comprising:

a nucleic acid amplification step of performing nucleic acid amplification reaction using a nucleic acid obtained from a sample to be analyzed as a template, and a primer set according to (13); and a detection step of detecting the nucleic acid amplification product in a product of the nucleic acid amplification reaction in the nucleic acid amplification step.

The present specification encompasses the contents disclosed in Japanese Patent Application No. 2016-132066 on which the priority of the present application is based.

By use of the primer set according to one or more embodiments of the present invention, an amplification product containing two or more target nucleic acids linked in series can be obtained. The detection of such an amplification product is easier than the individual detection of two or more target nucleic acids.

BRIEF DESCRIPTION OF DRAWINGS

FIGS. 1A to 1D show that the method according to one or more embodiments of the present invention detects an amplification product containing three target nucleic acids linked in series by labeling the amplification product and binding the amplification product onto a solid-phase support. In this case, positivity can be determined when the label is detected on the solid-phase support (FIG. 1A), and negativity can be determined when the label is not detected on the solid-phase support (FIG. 1B, FIG. 1C, and FIG. 1D). Therefore, the identification performance is high.

FIGS. 2A to 2D show that three target nucleic acids are individually amplified, and the amplification products are labeled, bound onto a solid-phase support, and detected. In this case, positivity is determined when the label is detected at 3 moieties on the solid-phase support (FIG. 2A), and negativity is determined when the label is not detected on the solid-phase support or when the label is detected at 1 or 2 moieties (FIG. 2B, FIG. 2C, and FIG. 2D). Identification may not be easy depending on the number or position of the label.

FIGS. 4A to 4D show diagrams for illustrating the function of a primer set of embodiment 2 (N=2).

FIGS. 5A and 5B show diagrams for illustrating the function of a primer set of embodiment 3 (N=2).

FIGS. 6A and 6B show diagrams for illustrating the function of a primer set of embodiment 4 (N=2).

DETAILED DESCRIPTION OF EMBODIMENTS

Figure 3A:
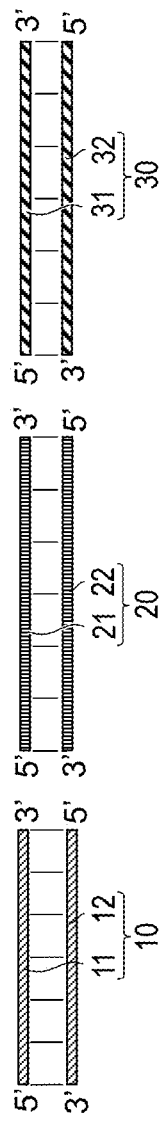
FIGS. 3A to 3C are diagrams for illustrating the function of a primer set of embodiment 1 (N=3).

Hereinafter, one or more embodiments of the present invention will be described in detail.

In one or more embodiments of the present invention, the terms "nucleic acid" and "polynucleotide" refer to DNA or RNA and are typically DNA. The terms "nucleic acid" and "polynucleotide" are not particularly limited by the number of bases and also include an oligonucleotide. In one or more embodiments of the present invention, an oligonucleotide that extends by that hybridizes to a target nucleic acid or a complementary strand of the target nucleic acid serving as a template in nucleic acid amplification reaction refers to an oligonucleotide capable of being double-stranded in nucleic acid amplification reaction and is typically a polymer of natural nucleotides, unless particularly limited. The natural nucleotide is a nucleotide constituted by a natural base adenine, thymine, guanine, cytosine, or uracil, a sugar moiety deoxyribose or ribose, and a phosphoric acid group, and is a nucleotide in which each moiety is not artificially modified. The natural nucleotide is usually a D-nucleotide. The D-nucleotide refers to a nucleotide with its sugar moiety consisting of D-deoxyribose or D-ribose.

In one or more embodiments of the present invention, the "target nucleic acid" includes not only a nucleic acid itself having a nucleotide sequence to be detected and/or amplified, but a nucleic acid having a nucleotide sequence complementary thereto. Therefore, in one or more embodiments of the present invention, the phrase "detecting a target nucleic acid" or "amplifying a target nucleic acid" includes not only detection or amplification intended for the target nucleic acid itself, but the detection or amplification of a complementary strand of the target nucleic acid or a double-stranded nucleic acid of the target nucleic acid through the detection or amplification of the target nucleic acid.

In one or more embodiments of the present invention, the term "nucleotide sequence of a target nucleic acid" or "target sequence" includes not only a nucleotide sequence to be detected and/or amplified, but a nucleotide sequence complementary thereto.

When the target nucleic acid is in a double-stranded form, the "nucleotide sequence of a target nucleic acid" or the "target sequence" refers to a nucleotide sequence contained in any one of the strands. The "target nucleic acid" may refer to one of the strands of a double-stranded target nucleic acid.

The full length of the target nucleic acid according to one or more embodiments of the present invention is not particularly limited and is usually a length of 20 bases or more, 40 bases or more, or 100 bases or more. The upper limit of the full length of the target nucleic acid is not particularly limited and is usually a length of 1000 bases or less, 500 bases or less or 400 bases or less.

In one or more embodiments of the present invention, the nucleic acid serving as a template in nucleic acid amplification reaction may be DNA or may be RNA. The nucleic acid may be a double-stranded nucleic acid or may be a single-stranded nucleic acid. The double-stranded nucleic acid can be single-stranded by denaturation treatment.

The nucleic acid serving as a template may be natural or may be artificially synthesized. The nucleic acid may be, for example, a natural nucleic acid extracted from a biological sample, may be a nucleic acid amplified by PCR or the like, or may be cDNA synthesized by reverse-transcription reaction.

In one or more embodiments of the present invention, the phrase "nucleotide sequence X "hybridizes" to nucleotide sequence Y" means that a polynucleotide (particularly, DNA) comprising the nucleotide sequence X hybridizes to a polynucleotide (particularly, DNA) comprising the nucleotide sequence Y under stringent conditions without hybridizing to a polynucleotide comprising no nucleotide sequence Y. In short, hybridizing refers to specifically hybridizing. In this context, the "stringent conditions" mean conditions under which a so-called specific hybrid is formed whereas any nonspecific hybrid is not formed, and can be appropriately determined with reference to, for example, Green and Sambrook, Molecular Cloning, 4th Ed (2012), Cold Spring Harbor Laboratory Press. Specifically, the stringent conditions can be set according to a temperature or a salt concentration of a solution for Southern hybridization, and a temperature or a salt concentration of a solution for a washing step of the Southern hybridization. More specifically, the stringent conditions involve a sodium concentration of 25 to 500 mM, preferably 25 to 300 mM, and a temperature of 40 to 68° C., preferably 40 to 65° C., for example, in a hybridization step. Further specifically, the hybridization can be performed at a temperature of 40° C. to 60° C. using 1 to 7×SSC and 0.02 to 3% SDS. A washing step may be performed after the hybridization. The washing step can be performed, for example, at a temperature of 50 to 65° C. using 0.1 to 2×SSC and 0.1 to 0.3% SDS. However, the hybridization between a tag for labeling and a polynucleotide-attached labeling agent mentioned later, and the hybridization between a tag for immobilization and a polynucleotide-attached solid-phase support mentioned later do not have to be performed under the stringent conditions listed here and can be performed under conditions mentioned later.

When nucleotide sequence X hybridizes to nucleotide sequence Y, the nucleotide sequence X and the nucleotide sequence Y can be combined such that a polynucleotide (particularly, DNA) comprising the nucleotide sequence X and a polynucleotide (particularly, DNA) comprising the nucleotide sequence Y can hybridize to each other under annealing conditions in nucleic acid amplification reaction to form a hydrogen bond sufficient for forming a stable duplex. These nucleotide sequences do not have to be completely complementary to each other. For example, a polynucleotide comprising the nucleotide sequence X and a polynucleotide comprising the nucleotide sequence Y may contain some mismatches such as 1 mismatch per 10 nucleotides, 1 mismatch per 20 nucleotides, or 1 mismatch per 30 nucleotides.

When nucleotide sequence X hybridizes to nucleotide sequence Y, one or more of the following relationships (A) to (C) are usually satisfied.

(A) a complementary sequence of the nucleotide sequence X and the nucleotide sequence Y are identical to each other. One of the complementary sequence of the nucleotide sequence X and the nucleotide sequence Y may be the nucleotide sequence of DNA, and the other sequence may be the nucleotide sequence of RNA. In this case, thymine in one of the sequences and uracil in the other sequence are regarded as identical bases.

(B) The nucleotide sequence Y is a nucleotide sequence derived from the complementary sequence of the nucleotide sequence X by the deletion, substitution, addition and/or insertion of one or several bases.

(C) The nucleotide sequence Y is a nucleotide sequence having 70% or higher identity to the complementary sequence of the nucleotide sequence X.

In the relationship (B), the term "one or several" refers to preferably 1 to 5, more preferably 1 to 4, still more preferably 1 to 3, particularly preferably 1 or 2 and is most preferably 1.

In the relationship (C), the value of identity refers to a value calculated at default settings using operation software (e.g., FASTA, DANASYS, and BLAST) for the identity between a plurality of nucleotide sequences. The value of identity between nucleotide sequences is calculated by calculating the number of matched bases between a pair of nucleotide sequences aligned so as to give the maximum degree of matches, and determining the ratio of this number of matched bases to the total number of bases in the compared nucleotide sequences. In this context, in the presence of a gap, the total number of bases described above is the number of bases including one gap counted as one base. For the detailed method for determining identity, see, for example, Altschul et al., Nuc. Acids. Res. 25, 3389-3402, 1977 and Altschul et al., J. Mol. Biol. 215, 403-410, 1990.

In the relationship (C), the identity is more preferably 80% or higher, still more preferably 90% or higher, yet still more preferably 95% or higher, further preferably 96% or higher, still further preferably 97% or higher, yet still further preferably 98% or higher, yet still further preferably 99% or higher identity.

In one or more embodiments of the present invention, methods for producing polynucleotides constituting a primer set, and primers comprising the polynucleotides and a linking polynucleotide are not particularly limited. These polynucleotides or primers may be produced through the use of a polynucleotide synthesis apparatus or may be produced through the use of custom synthesis service.

In one or more embodiments of the present invention, the "3'-terminal part" of a certain nucleotide sequence or polynucleotide refers to a partial nucleotide sequence consisting of a plurality of consecutive bases including the 3'-terminal base of the nucleotide sequence or the polynucleotide, or a region of a polynucleotide comprising the partial nucleotide sequence.

<1. Primer Set>

The primer set according to one or more embodiments of the present invention is a primer set that can produce, when a sample to be analyzed contains predetermined two or more target nucleic acids, a nucleic acid for detection comprising the predetermined two or more target nucleic acids, a labeling part which is a labeling agent or is a tag capable of binding to a labeling agent, and a binding part which is a tag capable of binding to a solid-phase support, in a linked form by nucleic acid amplification reaction using a nucleic acid obtained from the sample to be analyzed as a template.

The present specification discloses four embodiments of the primer set for achieving such a function.

In the description below, two or more target nucleic acids are set to N target nucleic acids from a first target nucleic acid to a Nth target nucleic acid. In this context, N is an integer of 2 or larger. The upper limit of N is not particularly limited and can be a number of 3, 4, 5, 6, 7, 8, 9, 10 or larger.

The nucleotide sequence of a polynucleotide contained in each component constituting each primer set can be designed so as not to inhibit the nucleic acid amplification reaction of interest with polynucleotides contained in the other components.

1.1. Embodiment 1 of Primer Set

Embodiment 1 of the primer set according to one or more embodiments of the present invention relates to a primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth double-headed primer comprising two polynucleotides linked at their 5' terminal sides, wherein one of the two polynucleotides comprises, in its 3'-terminal part, a nucleotide sequence that hybridizes to a 3'-terminal part of the nucleotide sequence of a kth target nucleic acid, and the other of the two polynucleotides comprises, in its 3'-terminal part, a nucleotide sequence that hybridizes to a 3'-terminal part of a complementary sequence of the nucleotide sequence of a (k+1)th target nucleic acid; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth double-headed primer involves the case where k is 1 to the case where k is N−1, and one of the terminal primer A and the terminal primer B further comprises a labeling part which is a labeling agent or is a tag capable of binding to a labeling agent, and the other terminal primer further comprises a binding part which is a tag capable of binding to a solid-phase support.

In the terminal primer A, the "nucleotide sequence that hybridizes to a 3'-terminal part of a complementary sequence of the nucleotide sequence of a first target nucleic acid" is not particularly limited by its length. The length can be, for example, 8 bases or more, 12 bases or more, or 15 bases or more and can be 40 bases or less, 30 bases or less, or 25 bases or less. The polynucleotide contained in the terminal primer A (polynucleotide other than a labeling part or a binding part mentioned later when the terminal primer A comprises a polynucleotide as the labeling part or the binding part) can comprise, in its 3'-terminal part, a nucleotide sequence that hybridizes to a 3'-terminal part of a complementary sequence of the nucleotide sequence of a first target nucleic acid, and an additional nucleotide sequence may be further added at the 5'-terminal side thereof. The full length of the polynucleotide contained in the terminal primer A is not particularly limited. The full length can be, for example, 8 bases or more, 12 bases or more, or 15 bases or more and can be 40 bases or less, 30 bases or less, or 25 bases or less.

In the kth double-headed primer, the "two polynucleotides linked at their 5' terminal sides" mean that the respective 3' ends of the two polynucleotides are in a liberated form, and the two polynucleotides are linked to each other at their 5' terminal sides. When the two polynucleotides are linked to each other at their 5' terminal sides, a structure that links the 5' ends is not particularly limited and can be constituted by an appropriate divalent group. Examples of the simplest structure include, but are not limited to, a 5'-5' bond in which the 5' positions of sugars on the respective 5'-terminal nucleotides of the two polynucleotides are bonded to each other via a phosphoric acid group. The divalent group may have a long-chain structure.

Other examples of the structure that links the respective 5' ends of the two polynucleotides in the kth double-headed primer can include fatty acid spacers given below.

Examples of the fatty acid spacer include a spacer represented by the following formula (II):

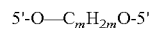  Formula (II)

wherein 5' represents an oxygen atom of the 5'-terminal phosphodiester bond of each polynucleotide, m represents an integer of 1 or larger and 40 or smaller, and H may be replaced with a substituent.

In the formula (II), m is preferably 2 or larger and 36 or smaller, more preferably 3 or larger and 16 or smaller. H in the formula (II) may be replaced with a substituent. Examples of the substituent typically include an alkyl group, an alkoxy group, and a hydroxy group. The number of carbon atoms in the alkyl group or the alkoxy group as the substituent is preferably 1 to 8, more preferably 1 to 4. In the case of having two or more substituents, the substituents may be the same or different. It is also preferred to have no substituent.

Alternative examples of the spacer include a spacer represented by the following formula (III):

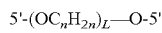

5'-(OC$_n$H$_{2n}$)$_L$—O-5'  Formula (III)

wherein 5' represents an oxygen atom of the 5'-terminal phosphodiester bond of each polynucleotide, n represents an integer of 2 or larger and 4 or smaller, L is an integer of 1 or larger and represents an integer that gives (n+1)×L=40 or smaller, and H may be replaced with a substituent.

In the formula (III), (n+1)×L is preferably 2 or larger and 36 or smaller, more preferably 3 or larger and 16 or less. The same form as that of the substituent in the formula (II) is applied to the substituent for H in the formula (III).

Other examples of the fatty acid spacer include the following divalent groups:

[Formula 1]

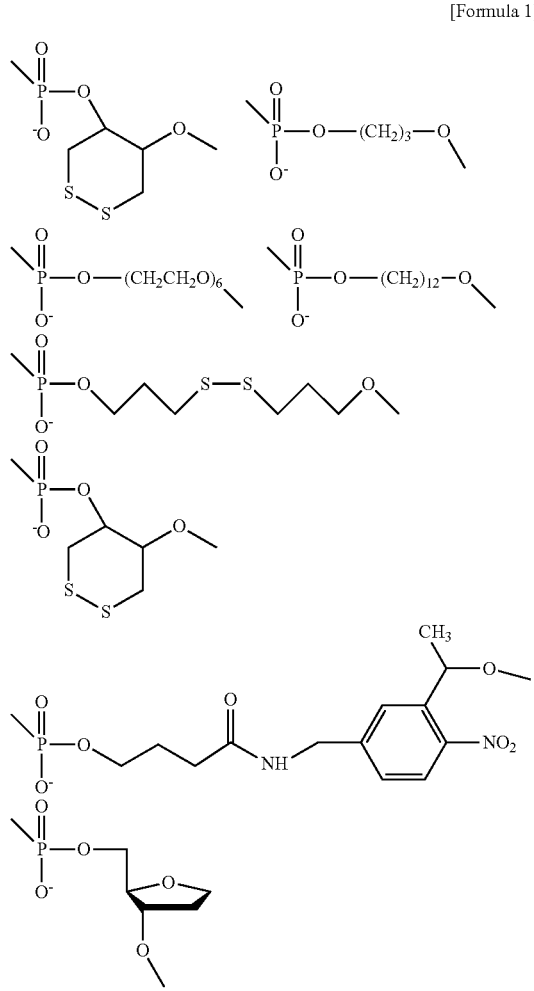

In the case of connecting the two polynucleotide molecules at their 5' ends via any of these divalent groups, the phosphoric acid group at one end of each divalent group refers to the phosphoric acid group of the 5'-terminal nucleotide of one of the polynucleotide molecules, and the oxygen atom at the other end forms a phosphoester bond with the phosphoric acid group of the 5'-terminal nucleotide of the other polynucleotide molecule.

The full lengths of the two polynucleotides contained in the kth double-headed primer are not particularly limited. Each of the full lengths can be, for example, 8 bases or more, 12 bases or more, or 15 bases or more and can be 40 bases or less, 30 bases or less, or 25 bases or less.

One of the two polynucleotides contained in the kth double-headed primer comprises, in its 3'-terminal part, a nucleotide sequence that hybridizes to a 3'-terminal part of the nucleotide sequence of a kth target nucleic acid. In this context, the "nucleotide sequence that hybridizes to a 3'-terminal part of the nucleotide sequence of a kth target nucleic acid" is not particularly limited by its length. The length can be, for example, 8 bases or more, 12 bases or more, or 15 bases or more and can be 40 bases or less, 30 bases or less, or 25 bases or less. The polynucleotide comprising, in its 3'-terminal part, the "nucleotide sequence that hybridizes to a 3'-terminal part of the nucleotide sequence of a kth target nucleic acid" can comprise this nucleotide sequence in its 3'-terminal part, and an additional nucleotide sequence may be further added at the 5'-terminal side thereof.

The other of the two polynucleotides contained in the kth double-headed primer comprises, in its 3'-terminal part, a nucleotide sequence that hybridizes to a 3'-terminal part of a complementary sequence of the nucleotide sequence of a (k+1)th target nucleic acid. In this context, the "nucleotide sequence that hybridizes to a 3'-terminal part of a complementary sequence of the nucleotide sequence of a (k+1)th target nucleic acid" is not particularly limited by its length. The length can be, for example, 8 bases or more, 12 bases or more, or 15 bases or more and can be 40 bases or less, 30 bases or less, or 25 bases or less. The polynucleotide comprising, in its 3'-terminal part, the "nucleotide sequence that hybridizes to a 3'-terminal part of a complementary sequence of the nucleotide sequence of a (k+1)th target nucleic acid" can comprise this nucleotide sequence in its 3'-terminal part, and an additional nucleotide sequence may be further added at the 5'-terminal side thereof.

In the terminal primer B, the "nucleotide sequence that hybridizes to a 3'-terminal part of the nucleotide sequence of a Nth target nucleic acid" is not particularly limited by its length. The length can be, for example, 8 bases or more, 12 bases or more, or 15 bases or more and can be 40 bases or less, 30 bases or less, or 25 bases or less. The polynucleotide contained in the terminal primer B (polynucleotide other than a labeling part or a binding part mentioned later when the terminal primer B comprises a polynucleotide as the labeling part or the binding part) can comprise, in its 3'-terminal part, a nucleotide sequence that hybridizes to a 3'-terminal part of the nucleotide sequence of a Nth target nucleic acid, and an additional nucleotide sequence may be further added at the 5'-terminal side thereof. The full length of the polynucleotide contained in the terminal primer B is not particularly limited. The full length can be, for example, 8 bases or more, 12 bases or more, or 15 bases or more and can be 40 bases or less, 30 bases or less, or 25 bases or less.

One of the terminal primer A and the terminal primer B further comprises the labeling part, and the other terminal primer further comprises the binding part, in addition to the polynucleotides described above.

Each of the terminal primer A and the terminal primer B has one of the labeling part and the binding part. The labeling part and the binding part are chemically linked to the polynucleotide, if necessary, via an appropriate spacer mentioned later. In the terminal primer A and the terminal primer B, the position at which one of the labeling part and the binding part is linked to the polynucleotide is not particularly limited as long as the position does not inhibit the annealing between the polynucleotide and a target nucleic acid or a nucleic acid complementary to the target nucleic acid, and extension through polymerase reaction. The position is preferably the 5' end of the polynucleotide.

Hereinafter, the labeling part and the binding part used in one or more embodiments of the present invention will be described in detail.

The labeling part is either a tag capable of binding to a labeling agent or a labeling agent and is preferably a tag capable of binding to a labeling agent. In the present specification, the tag capable of binding to a labeling agent is also referred to as a tag for labeling. When the labeling part is a tag for labeling, the tag contained at one end of an amplification product of nucleic acid amplification reaction can be labeled by contacting the amplification product with a labeling agent. When the labeling part is a labeling agent, an amplification product containing the labeling agent at one end can be obtained as an amplification product of nucleic acid amplification reaction.

The labeling agent is not particularly limited as long as the labeling agent permits detection of an amplification product. The labeling agent preferably permits visual detection of an amplification product. Examples of such a labeling agent include coloring particles, dyes, and enzymes (peroxidase, alkaline phosphatase, luciferase, etc.). The labeling agent is preferably a coloring particle. Examples of the "coloring particle" include, but are not limited to, metal (e.g., gold, silver, copper, and platinum) particles, metal rods, colored latex particles, and silica nanoparticles containing a dye. The labeling agent can have any size that does not interfere with capture of an amplification product onto a solid-phase support mentioned later. The labeling agent preferably produces great color for detection and can be appropriately selected so as to have a size smaller than the pore sizes of porous members in a solid-phase support or a nucleic acid detection device mentioned later. The size of the labeling agent can be a particle size of, for example, approximately 500 nm or smaller, preferably approximately 0.1 nm to 250 nm, more preferably approximately 1 nm to 100 nm. A fluorescent dye (fluorescein, cyanine, etc.) or the like may be used as the dye. In this case, it is preferred to perform detection by irradiation with light at an excitation wavelength of each fluorescent dye.

The tag for labeling that may be used as the labeling part can be any tag that is capable of binding to a labeling agent and is not double-stranded by extension in nucleic acid amplification reaction. The tag for labeling can be appropriately selected according to the structure of the labeling agent and is not particularly limited. For example, a tag consisting of a polynucleotide (DNA, RNA, etc.), a protein, a peptide, or any of other compounds (e.g., low-molecular compounds such as biotin, fluorescein isothiocyanate (FITC), and digoxigenin (DIG)), or a combination thereof can be used.

One preferred form of the tag for labeling comprises a polynucleotide or consists of a polynucleotide. The polynucleotide that may be contained in the tag for labeling is not particularly limited as long as the polynucleotide does not substantially hinder nucleic acid amplification reaction with the primer set according to one or more embodiments of the present invention. The polynucleotide is, for example, a polynucleotide having 5 to 50, preferably 10 to 35 bases. Preferred examples thereof can include a polynucleotide comprising a nucleotide sequence described in Anal. Biochem. 364 (2007), 78-85. Another preferred form of the tag for labeling consists of a low-molecular compound such as biotin, FITC, or DIG.

When the labeling part is the tag for labeling described above, the binding between the labeling agent and the tag for labeling may be direct binding or may be indirect binding. A suitable binding approach can be appropriately selected according to the combination of the labeling agent and the tag for labeling used. For example, when the tag for labeling comprises a polynucleotide, the labeling agent is bound to a polynucleotide capable of hybridizing to the polynucleotide of the tag (e.g., a polynucleotide comprising a sequence complementary to the nucleotide sequence of the polynucleotide of the tag), and these polynucleotides can be hybridized to each other to indirectly bind the labeling agent to the tag for labeling. The binding between the labeling agent and the polynucleotide may be performed via a peptide, a protein, a nucleic acid, or the like or may be performed via an appropriate functional group. The hybridization conditions can be conditions resulting in hybridization and are not particularly limited. The hybridization can be performed through reaction, for example, at 20° C. to 40° C. in a buffer solution containing 10 mM to 50 mM phosphoric acid (pH 6 to 7). The buffer solution can further contain a salt such as sodium chloride in order to enhance hybridization efficiency.

When the tag for labeling is a low-molecular compound, the tag can be labeled with a labeling agent linked to a binding material, such as a protein (e.g., avidin binding to biotin, or a protein binding to FITC), an antibody (e.g., an anti-DIG antibody), or an aptamer, specifically binding to the low-molecular compound. In this case, the tag for labeling and the binding material can be bound to each other using any of various buffer solutions of near neutral pH.

The labeling part (tag for labeling or labeling agent) and the polynucleotide contained in the terminal primer A or B can be bound to each other directly or indirectly by an arbitrary approach. However, when at least a moiety to be connected with the polynucleotide consists of a polynucleotide in the labeling part, the moiety has a structure that is not double-stranded by extension in nucleic acid amplification reaction.

A polynucleotide potentially capable of serving as a template in reaction mediated by DNA polymerase (usually, a polynucleotide consisting of natural nucleotides) may be used as the polynucleotide that is contained in the labeling part and is not double-stranded by nucleic acid amplification reaction. In this case, the polynucleotide contained in the labeling part and the polynucleotide functioning as a primer in the terminal primer A or B are bound to each other via a spacer that inhibits polymerase reaction. Such a "spacer" can be any spacer that can suppress or stop the progression of polymerase (DNA polymerase, etc.) reaction in nucleic acid amplification reaction and prevents the labeling part from being double-stranded. Examples thereof include, but are not limited to, nucleic acid sequences having a robust hairpin structure or pseudoknot structure, nucleic acids in a L form, peptide nucleic acid (PNA), bridged nucleic acid (BNA) or locked nucleic acid (LNA), fluorescein, Cy3, Cy5, divalent groups having an azobenzene structure represented by the following formula I, aliphatic chains (alkylene chains and polyoxyalkylene chains), and divalent groups having an inverted sequence structure such as a 5'-5' bond or a 3'-3' bond. The polynucleotide contained in the labeling part and the polynucleotide functioning as a primer in the terminal primer A or B, when linked via the spacer described above, can be linked in the same direction. In short, the 3' end of the polynucleotide contained in the labeling part and the 5' end of the polynucleotide functioning as a primer in the terminal primer A or B can be linked to each other via the spacer described above.

[Formula 2]

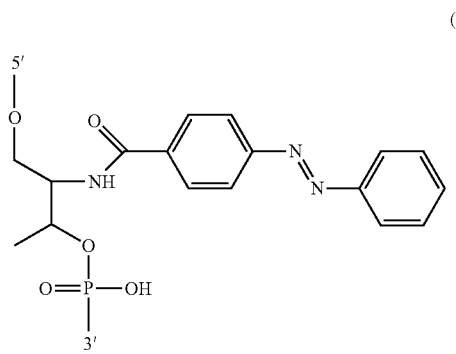

(Formula I)

In the case of connecting the two polynucleotide molecules via the divalent group represented by formula I, the phosphoric acid group at one end (3' end) of the divalent group refers to the phosphoric acid group of the 5'-terminal nucleotide of one of the polynucleotide molecules, and the oxygen atom at the other end (5' end) forms a phosphoester bond with the phosphoric acid group of the 3'-terminal nucleotide of the other polynucleotide molecule.

Examples of the fatty acid spacer include a spacer represented by the following formula (IV):

$$5'\text{-O--}C_mH_{2m}\text{--O-}3' \quad \text{Formula (IV)}$$

wherein 5' represents an oxygen atom of a 5'-phosphodiester bond, 3' represents an oxygen atom of a 3'-phosphodiester bond, m represents an integer of 1 or larger and 40 or smaller, and H may be replaced with a substituent.

In the formula (IV), m is preferably 2 or larger and 36 or smaller, more preferably 3 or larger and 16 or smaller. H in the formula (IV) may be replaced with a substituent. Examples of the substituent typically include an alkyl group, an alkoxy group, and a hydroxy group. The number of carbon atoms in the alkyl group or the alkoxy group as the substituent is preferably 1 to 8, more preferably 1 to 4. In the case of having two or more substituents, the substituents may be the same or different. It is also preferred to have no substituent.

Alternative examples of the spacer include a spacer represented by the following formula (V):

$$5'\text{-}(OC_nH_{2n})_L\text{--O-}3' \quad \text{Formula (V)}$$

wherein 5' represents an oxygen atom of a 5'-phosphodiester bond, 3' represents an oxygen atom of a 3'-phosphodiester bond, n represents an integer of 2 or larger and 4 or smaller, L is an integer of 1 or larger and represents an integer that gives $(n+1) \times L = 40$ or smaller, and H may be replaced with a substituent.

In the formula (V), $(n+1) \times L$ is preferably 2 or larger and 36 or smaller, more preferably 3 or larger and 16 or smaller. The same form as that of the substituent in the formula (IV) is applied to the substituent for H in the formula (V).

When the two polynucleotide molecules are bound to each other through a 5'-5' bond, the fatty acid spacer represented by the formula (II) or the formula (III) described above can be used.

Other examples of the fatty acid spacer include the following divalent groups:

[Formula 3]

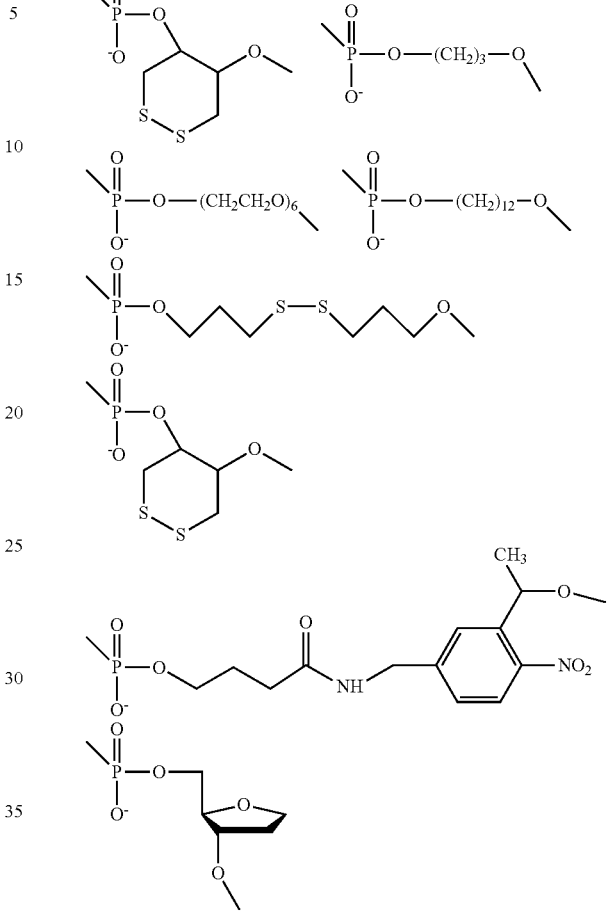

In the case of connecting the two polynucleotide molecules via any of these divalent groups, the phosphoric acid group at one end of each divalent group refers to the phosphoric acid group of the 3'-terminal or 5'-terminal nucleotide of one of the polynucleotide molecules, and the oxygen atom at the other end forms a phosphoester bond with the phosphoric acid group of the 5'-terminal or 3'-terminal nucleotide of the other polynucleotide molecule.

On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide contained in the labeling part. In this case, the spacer described above that inhibits polymerase reaction may be omitted.

Next, the binding part used in one or more embodiments of the present invention will be described.

The binding part is a tag capable of binding to a solid-phase support mentioned later. In the present specification, the tag capable of binding to a solid-phase support is also referred to as a tag for immobilization.

The tag for immobilization that may be used as the binding part can be any tag that is capable of binding to a solid-phase support. The tag for immobilization can be appropriately selected according to the structure of the solid-phase support and is not particularly limited. For example, a tag consisting of a polynucleotide (DNA, RNA, etc.), a protein, a peptide, or any of other compounds (e.g., low-molecular compounds as described above), or a combination thereof can be used. The tag for immobilization preferably comprises a polynucleotide or consists of a polynucleotide. The polynucleotide that may be contained in the tag for immobilization is not particularly limited as long as the polynucleotide does not substantially hinder nucleic acid amplification reaction with the primer set in one or more embodiments of the present invention. The polynucleotide is, for example, a polynucleotide having 5 to 50, preferably 10 to 35 bases. Preferred examples thereof can include a polynucleotide comprising a nucleotide sequence described in Anal. Biochem. 364 (2007), 78-85.

In the case of using a polynucleotide as the tag for immobilization, its combination with a polynucleotide that is disposed on the solid-phase support side and comprises a nucleotide sequence that hybridizes to the polynucleotide can be easily changed by engineering the nucleotide sequence. This is preferred because binding specificity is easily controlled. For example, when a plurality of nucleic acid amplification products are bound onto one solid-phase support and each discriminated, a distinct combination of the tag for immobilization and the solid-phase support-side polynucleotide is necessary for each nucleic acid amplification product. The nucleotide sequence of a polynucleotide is easily changed, and the hybridization between polynucleotides has high binding specificity. Hence, use of a polynucleotide as the tag for immobilization facilitates providing a distinct combination of the tag for immobilization and the solid-phase support-side polynucleotide for each nucleic acid amplification product.

The solid-phase support is not particularly limited. The solid-phase support used can be made of a resin, a metal, a polysaccharide, a mineral, or the like and can be in a form such as a membrane, a film, a nonwoven fabric, a plate, or a gel. Preferably, the solid-phase support has a porous structure such that an amplification product or the labeling agent can be developed in a solution. Examples of the solid-phase support that may be used in one or more embodiments of the present invention include filter papers, nitrocellulose membranes, polyethersulfone membranes, nylon membranes, various dried gels (silica gel, agarose gel, dextran gel, and gelatin gel), silicon, glass, and plastics. The size and form of the solid-phase support can be appropriately selected as appropriate ones for various operations or detection.

At least a partial moiety of the solid-phase support can be configured to be capable of binding to the tag for immobilization. More preferably, only the partial moiety is configured to be capable of binding to the tag for immobilization. Only the particular moiety of the solid-phase support is configured to be capable of binding to the tag for immobilization, whereby an amplification product captured by the solid-phase support is detected in a manner localized only to the moiety. Hence, positivity or negativity can be easily identified.

The binding between the solid-phase support and the tag for immobilization may be direct binding or may be indirect binding. A suitable binding approach can be appropriately selected according to the combination of the solid-phase support and the tag for immobilization used. For example, when the tag for immobilization comprises a polynucleotide, a polynucleotide capable of hybridizing to the polynucleotide of the tag (e.g., a polynucleotide comprising a sequence complementary to the nucleotide sequence of the polynucleotide of the tag) is immobilized onto the solid-phase support to form a tag capture unit, and these polynucleotides can be hybridized to each other to indirectly bind the solid-phase support and the tag for immobilization. The immobilization of the polynucleotide onto the solid-phase support may be performed via a peptide, a protein, a nucleic acid, or the like or may be performed via an appropriate functional group. The hybridization conditions can be the conditions described above about the binding between the tag for labeling and the labeling agent. When the polynucleotide is immobilized onto the solid-phase support, the polynucleotide is immobilized in a manner localized to a particular moiety, whereby a captured amplification product is detected in a manner localized only to the predetermined moiety. Hence, positivity or negativity can be easily identified.

The binding part (tag for immobilization) and the polynucleotide functioning as a primer contained in the terminal primer A or B can be bound to each other directly or indirectly by an arbitrary approach. However, at least a moiety to be connected with the polynucleotide, in the tag for immobilization may consist of a polynucleotide capable of serving as a template in reaction mediated by DNA polymerase. In this case, the polynucleotide and the tag for immobilization are bound to each other via a "spacer" that inhibits polymerase reaction so as not to double-strand the moiety, together with the polynucleotide functioning as a primer, by extension in nucleic acid amplification reaction. Specific examples of the spacer to be provided between the binding part comprising the polynucleotide capable of serving as a template in reaction mediated by DNA polymerase and the polynucleotide contained in the terminal primer A or B are the same as those mentioned above about the spacer to be provided between the labeling part comprising a polynucleotide and the polynucleotide. On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide contained in the tag for immobilization. In this case, the spacer described above that inhibits polymerase reaction may be omitted.

The case of using first target nucleic acid 11, second target nucleic acid 21, and third target nucleic acid 31 as three target nucleic acids (i.e., N=3) will be taken as an example, and the function of the primer set of embodiment 1 will be described with reference to FIG. 3.

In the example shown in FIG. 3, the first target nucleic acid 11 forms first target nucleic acid 10 in a double-stranded form (double-stranded first target nucleic acid) together with first target nucleic acid-complementary strand 12 which is a complementary strand thereof. Any of the first target nucleic acid 11 and the first target nucleic acid-complementary strand 12 may be an object to be amplified and detected.

Likewise, the second target nucleic acid 21 forms double-stranded second target nucleic acid 20 together with second target nucleic acid-complementary strand 22 which is a complementary strand thereof.

Likewise, the third target nucleic acid 31 forms double-stranded third target nucleic acid 30 together with third target nucleic acid-complementary strand 32 which is a complementary strand thereof.

Terminal primer A 100 comprises polynucleotide 101 comprising, in its 3'-terminal part, a nucleotide sequence that hybridizes to a 3'-terminal part of complementary sequence 12 (which refers to the nucleotide sequence of the first target nucleic acid-complementary strand 12) of first target sequence 11 (which refers to the nucleotide sequence of the first target nucleic acid 11). The terminal primer A 100 further has terminal primer A added moiety 102, in addition to the polynucleotide 101. The terminal primer A added moiety 102 is any one of the labeling part and the binding part.

The example of FIG. 3 involves first double-headed primer 110 and second double-headed primer 120 as the kth double-headed primers because of N=3.

The first double-headed primer 110 comprises first polynucleotide 111 of the first double-headed primer and second polynucleotide 112 of the first double-headed primer which are two polynucleotides linked to each other at their 5' terminal sides. The first polynucleotide 111 of the first double-headed primer comprises, in its 3'-terminal part, a nucleotide sequence that hybridizes to a 3'-terminal part of the nucleotide sequence of the first target nucleic acid 11. The second polynucleotide 112 of the first double-headed primer comprises, in its 3'-terminal part, a nucleotide sequence that hybridizes to a 3'-terminal part of the nucleotide sequence of the complementary strand 22 of the second target nucleic acid 21.

The second double-headed primer 120 comprises first polynucleotide 121 of the second double-headed primer and second polynucleotide 122 of the second double-headed primer which are two polynucleotides linked to each other at their 5' terminal sides. The first polynucleotide 121 of the second double-headed primer comprises, in its 3'-terminal part, a nucleotide sequence that hybridizes to a 3'-terminal part of the nucleotide sequence of the second target nucleic acid 21. The second polynucleotide 122 of the second double-headed primer comprises, in its 3'-terminal part, a nucleotide sequence that hybridizes to a 3'-terminal part of the nucleotide sequence of the complementary strand 32 of the third target nucleic acid 31.

Terminal primer B 130 comprises polynucleotide 131 comprising, in its 3'-terminal part, a nucleotide sequence that hybridizes to a 3'-terminal part of the nucleotide sequence of the third target nucleic acid 31. The terminal primer B 130 further has terminal primer B added moiety 132 in addition to the polynucleotide 131. The terminal primer B added moiety 132 is any one of the labeling part and the binding part.

Figure 3B:
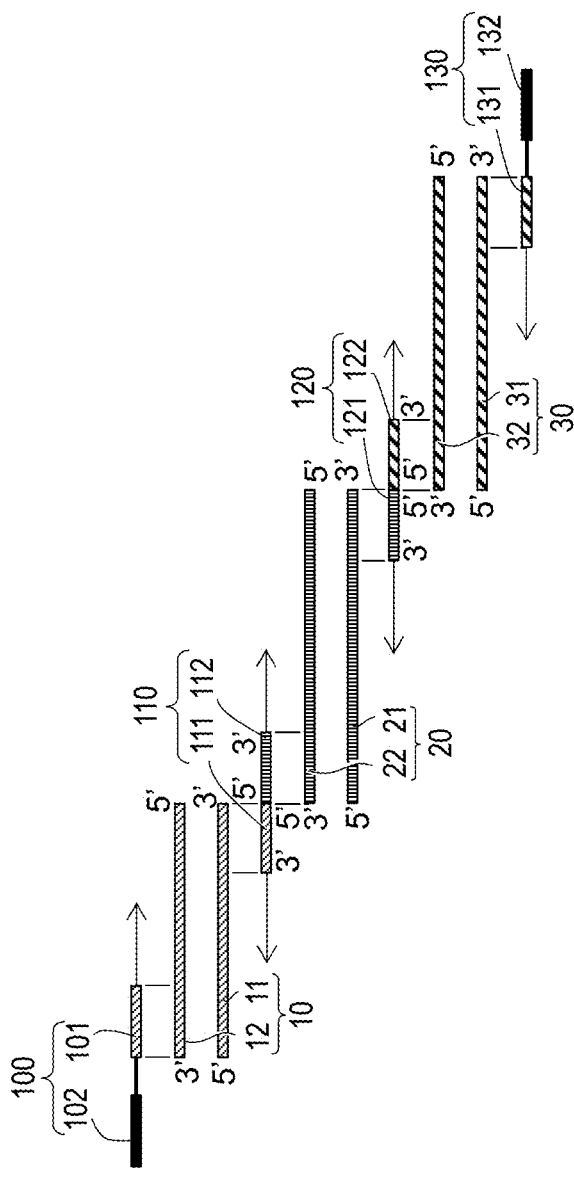

As shown in FIG. 3B, nucleic acid amplification reaction is performed using the nucleic acids as a template in the presence of the primer set of the embodiment 1 comprising the terminal primer A 100, the first double-headed primer 110, the second double-headed primer 120 and the terminal primer B 130. In this reaction, the polynucleotide 101 of the terminal primer A 100 hybridizes to the 3'-terminal part of the first target nucleic acid-complementary strand 12 through denaturation and annealing. Extension reaction mediated by polymerase synthesizes amplified fragment 301 of the first target nucleic acid 11 linked at its 5' end to the terminal primer A added moiety 102. Also, the first polynucleotide 111 of the first double-headed primer hybridizes to the 3'-terminal part of the first target nucleic acid 11 through denaturation and annealing. Extension reaction mediated by polymerase synthesizes an amplified fragment of the first target nucleic acid-complementary strand 12. This amplified fragment of the first target nucleic acid-complementary strand 12 is linked at its 5' end to the 5' end of an amplified fragment of the second target nucleic acid 21 synthesized by the extension of the second polynucleotide 112 of the first double-headed primer as mentioned later and integrally constitutes one amplified fragment 302.

Likewise, as shown in FIG. 3B, the second polynucleotide 112 of the first double-headed primer hybridizes to the 3'-terminal part of the second target nucleic acid-complementary strand 22 through denaturation and annealing. Extension reaction mediated by polymerase synthesizes an amplified fragment of the second target nucleic acid 21. This amplified fragment constitutes a portion of the amplified fragment 302 described above. Also, the first polynucleotide 121 of the second double-headed primer hybridizes to the 3'-terminal part of the second target nucleic acid 21 through denaturation and annealing. Extension reaction mediated by polymerase synthesizes an amplified fragment of the second target nucleic acid-complementary strand 22. This amplified fragment of the second target nucleic acid-complementary strand 22 is linked at its 5' end to the 5' end of an amplified fragment of the third target nucleic acid 31 synthesized by the extension of the second polynucleotide 122 of the second double-headed primer as mentioned later and integrally constitutes one amplified fragment 303.

Likewise, as shown in FIG. 3B, the second polynucleotide 122 of the second double-headed primer hybridizes to the 3'-terminal part of the third target nucleic acid-complementary strand 32 through denaturation and annealing. Extension reaction mediated by polymerase synthesizes an amplified fragment of the third target nucleic acid 31. This amplified fragment constitutes a portion of the amplified fragment 303 described above. Also, the polynucleotide 131 of the terminal primer B 130 hybridizes to the 3'-terminal part of the third target nucleic acid 31 through denaturation and annealing. Extension reaction mediated by polymerase synthesizes amplified fragment 304 of the third target nucleic acid-complementary strand 32 linked at its 5' end to the terminal primer B added moiety 132.

Figure 3C:
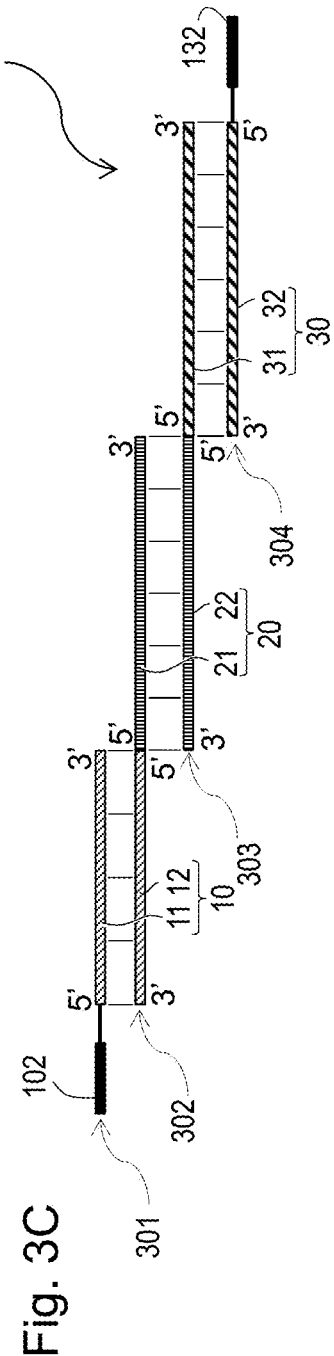

Further denaturation and annealing produce, as an amplification product, nucleic acid amplification product 1 in which, as shown in FIG. 3C, the double-stranded first target nucleic acid 10 containing the first target nucleic acid 11, the double-stranded second target nucleic acid 20 containing the second target nucleic acid 21, and the double-stranded third target nucleic acid 30 containing the third target nucleic acid 31 are linked in series, the terminal primer A added moiety 102 is linked at the 5'-terminal side of the first target nucleic acid 11, and the terminal primer B added moiety 132 is linked at the 5'-terminal side of the third target nucleic acid-complementary strand 32. The nucleic acid amplification product 1 can be immobilized onto a solid-phase support via the binding part contained in one of the terminal primer A added moiety 102 and the terminal primer B added moiety 132, and is detectable with the labeling part contained in the other added moiety as an index.

The nucleic acid amplification product 1 is obtained only when all three of the first target nucleic acid 11 (or the first target nucleic acid-complementary strand 12), the second target nucleic acid 21 (or the second target nucleic acid-complementary strand 22), and the third target nucleic acid 31 (or the third target nucleic acid-complementary strand 32) are present in a template. If one or two of these target nucleic acids or complementary strands thereof are absent in a template, only the target nucleic acid or the complementary strand thereof present therein is amplified whereas a nucleic acid amplification product having both the binding part and the labeling part is not produced. Thus, negativity is obtained in detection using the labeling part as an index. Hence, the risk of determining false positivity is very low.

The above description is not limited by the case of N=3 and holds true for all the cases where N is 2 or more.

As mentioned above, the nucleic acid amplification reaction using the primer set according to embodiment 1 produces a nucleic acid amplification product comprising:
an amplified fragment of a first target nucleic acid;
an amplified fragment in which a moiety of a complementary strand of a kth target nucleic acid and a moiety of a (k+1)th target nucleic acid are linked to each other at their 5' ends; and
an amplified fragment of a complementary strand of a Nth target nucleic acid, wherein
the first target nucleic acid to the Nth target nucleic acid each hybridize to a complementary strand thereof to form a duplex,
one of the amplified fragment of the first target nucleic acid and the amplified fragment of the complementary strand of the Nth target nucleic acid is linked at its 5' end to the labeling part, and
the other of the amplified fragment of the first target nucleic acid and the amplified fragment of the complementary strand of the Nth target nucleic acid is linked at its 5' end to the binding part.

In this context, N is an integer of 2 or larger, and k is an integer from 1 to N−1. In this nucleic acid amplification product, the structure of the linkage between the double-stranded nucleic acid containing the kth target nucleic acid and the double-stranded nucleic acid containing the (k+1)th target nucleic acid is the same as the structure of the linkage between the two polynucleotides in the kth double-headed primer.

1.2. Embodiment 2 of Primer Set

Embodiment 2 of the primer set according to one or more embodiments of the present invention relates to a primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth reverse primer comprising a polynucleotide which comprises, in its 3'-terminal part, nucleotide sequence $A_k$ that hybridizes to a 3'-terminal part of the nucleotide sequence of a kth target nucleic acid and further comprises nucleotide sequence $B_k$ at the 5'-terminal side of the nucleotide sequence $A_k$;

a (k+1)th forward primer comprising a polynucleotide which comprises, in its 3'-terminal part, nucleotide sequence $C_{k+1}$ that hybridizes to a 3'-terminal part of a complementary sequence of the nucleotide sequence of a (k+1)th target nucleic acid and further comprises nucleotide sequence $D_{k+1}$ that hybridizes to the nucleotide sequence $B_k$ at the 5'-terminal side of the nucleotide sequence $C_{k+1}$; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger,
k is an integer from 1 to N−1,
the kth reverse primer and the (k+1)th forward primer each involve the case where k is 1 to the case where k is N−1, and
one of the terminal primer A and the terminal primer B further comprises the labeling part, and the other terminal primer further comprises the binding part.

In the primer set of embodiment 2, the terminal primer A and the terminal primer B, the labeling part and the binding part, and structures that link them are the same as in embodiment 1, so that the description will be omitted.

In the kth reverse primer, the nucleotide sequence $A_k$ and the nucleotide sequence $B_k$ are not particularly limited by their lengths. Each of the lengths can be, for example, 8 bases or more, 12 bases or more, or 15 bases or more and can be 40 bases or less, 30 bases or less, or 25 bases or less. The polynucleotide comprising the nucleotide sequence $A_k$ and the nucleotide sequence $B_k$ can comprise the nucleotide sequence $A_k$ in its 3'-terminal part and comprise the nucleotide sequence $B_k$ upstream from the 5'-terminal base of the nucleotide sequence $A_k$, and an additional nucleotide sequence may be further added to each of between the nucleotide sequence $A_k$ and the nucleotide sequence $B_k$, and upstream from the nucleotide sequence $B_k$. The full length of the polynucleotide contained in the kth reverse primer is not particularly limited and can be, for example 80 bases or less, 60 bases or less, or 50 bases or less.

The polynucleotide constituting the kth reverse primer comprises the nucleotide sequence $A_k$ and the nucleotide sequence $B_k$ (and the additional nucleotide sequence described above, if present) in the same direction. The whole polynucleotide from the 5' end to the 3' end is capable of hybridizing to a polynucleotide comprising a complementary nucleotide sequence and has no configuration that inhibits polymerase reaction. Therefore, the polynucleotide constituting the kth reverse primer can be double-stranded as a whole by extension in nucleic acid amplification reaction.

In the (k+1)th forward primer, the nucleotide sequence $C_{k+1}$ and the nucleotide sequence $D_{k+1}$ are not particularly limited by their lengths. Each of the lengths can be, for example, 8 bases or more, 12 bases or more, or 15 bases or more and can be 40 bases or less, 30 bases or less, or 25 bases or less. The polynucleotide comprising the nucleotide sequence $C_{k+1}$ and the nucleotide sequence $D_{k+1}$ can comprise the nucleotide sequence $C_{k+1}$ in its 3'-terminal part and comprise the nucleotide sequence $D_{k+1}$ upstream from the 5'-terminal base of the nucleotide sequence $C_{k+1}$, and an additional nucleotide sequence may be further added to each of between the nucleotide sequence $C_{k+1}$ and the nucleotide sequence $D_{k+1}$, and upstream from the nucleotide sequence $C_{k+1}$. The full length of the polynucleotide contained in the (k+1)th forward primer is not particularly limited and can be, for example 80 bases or less, 60 bases or less, or 50 bases or less.

The polynucleotide constituting the (k+1)th forward primer comprises the nucleotide sequence $C_{k+1}$ and the nucleotide sequence $D_{k+1}$ (and the additional nucleotide sequence described above, if present) in the same direction. The whole polynucleotide from the 5' end to the 3' end is capable of hybridizing to a polynucleotide comprising a complementary nucleotide sequence and has no configuration that inhibits polymerase reaction. Therefore, the polynucleotide constituting the (k+1)th forward primer can be double-stranded as a whole by extension in nucleic acid amplification reaction.

The nucleotide sequence $B_k$ of the kth reverse primer and the nucleotide sequence $D_{k+1}$ of the (k+1)th forward primer are designed such that these nucleotide sequences are capable of hybridizing to each other.

The case of using first target nucleic acid 11 and second target nucleic acid 21 as two target nucleic acids (i.e., N=2) will be taken as an example, and the function of the primer set of embodiment 2 will be described with reference to FIG. 4.

Terminal primer A 200 comprises polynucleotide 201 comprising, in its 3'-terminal part, a nucleotide sequence that hybridizes to a 3'-terminal part of the nucleotide sequence of complementary strand 12 of the first target nucleic acid 11. The terminal primer A 200 further has terminal primer A added moiety 202 in addition to the polynucleotide 201. The terminal primer A added moiety 202 is any one of the labeling part and the binding part.

The example of FIG. 4 involves first reverse primer 210 as the kth reverse primer and second forward primer 220 as the (k+1)th forward primer because of N=2.

The first reverse primer 210 comprises a polynucleotide which comprises, in its 3'-terminal part, nucleotide sequence $A_1$ 211 (which refers to partial polynucleotide 211 comprising nucleotide sequence $A_1$ in the polynucleotide contained in the first reverse primer 210) that hybridizes to a 3'-terminal part of the nucleotide sequence of the first target nucleic acid 11 and further comprises nucleotide sequence $B_1$ 212 (which refers to partial polynucleotide 212 comprising nucleotide sequence $B_1$ in the polynucleotide contained in the first reverse primer 210) at the 5'-terminal side of the nucleotide sequence $A_1$ 211.

The second forward primer 220 comprises a polynucleotide which comprises, in its 3'-terminal part, nucleotide sequence $C_2$ 221 (which refers to partial polynucleotide 221 comprising nucleotide sequence $C_2$ in the polynucleotide contained in the second forward primer 220) that hybridizes to a 3'-terminal part of the nucleotide sequence of complementary strand 22 of the second target nucleic acid 21 and further comprises nucleotide sequence $D_2$ 222 (which refers to partial polynucleotide 222 comprising nucleotide sequence $D_2$ in the polynucleotide contained in the second forward primer 220) that hybridizes to the nucleotide sequence B 211 at the 5'-terminal side of the nucleotide sequence $C_2$ 221.

Terminal primer B 230 comprises polynucleotide 231 comprising, in its 3'-terminal part, a nucleotide sequence that hybridizes to a 3'-terminal part of the nucleotide sequence of the second target nucleic acid 21. The terminal primer B 230 further has terminal primer B added moiety 232 in addition to the polynucleotide 231. The terminal primer B added moiety 232 is any one of the labeling part and the binding part.

As shown in FIG. 4A, nucleic acid amplification reaction is performed using the nucleic acids as a template in the presence of the primer set of the embodiment 2 comprising the terminal primer A 200, the first reverse primer 210, the second forward primer 220 and the terminal primer B 230. In this reaction, the polynucleotide 201 of the terminal primer A 200 hybridizes to the 3'-terminal part of the first target nucleic acid-complementary strand 12 through denaturation and annealing. Extension reaction mediated by polymerase synthesizes amplified fragment 401 of the first target nucleic acid 11 linked at its 5' end to the terminal primer A added moiety 202. Also, the first reverse primer 210 hybridizes to the 3'-terminal part of the first target nucleic acid 11 through denaturation and annealing. Extension reaction mediated by polymerase synthesizes amplified fragment 402 containing the nucleotide sequence $B_1$ 212 positioned in the 5'-terminal part and the first target nucleic acid-complementary strand 12 positioned at the 3'-terminal side thereof.

Likewise, as shown in FIG. 4A, the second forward primer 220 hybridizes to the 3'-terminal part of the second target nucleic acid-complementary strand 22 through denaturation and annealing. Extension reaction mediated by polymerase synthesizes amplified fragment 403 containing the nucleotide sequence $D_2$ 222 positioned in the 5'-terminal part and the second target nucleic acid 21 positioned at the 3'-terminal side thereof.

Likewise, as shown in FIG. 4A, the polynucleotide 231 of the terminal primer B 230 hybridizes to the 3'-terminal part of the second target nucleic acid 21 through denaturation and annealing. Extension reaction mediated by polymerase synthesizes amplified fragment 404 of the second target nucleic acid-complementary strand 22 linked at its 5' end to the terminal primer B added moiety 232.

As shown in FIG. 4B, the moiety of the first target nucleic acid 11 of the amplified fragment 401 hybridizes to the moiety of the first target nucleic acid-complementary strand 12 of the amplified fragment 402 through further denaturation and annealing. Extension reaction mediated by polymerase synthesizes amplified fragment 405 containing the nucleotide sequence $D_2$ 222 positioned in the 3'-terminal part, the first target nucleic acid 11 positioned at the 5'-terminal side thereof, and the terminal primer A added moiety 202 linked to the 5' end.

Likewise, as shown in FIG. 4B, the moiety of the second target nucleic acid-complementary strand 22 of the amplified fragment 404 hybridizes to the moiety of the second target nucleic acid 21 of the amplified fragment 403. Extension reaction mediated by polymerase synthesizes amplified fragment 406 containing the nucleotide sequence $B_1$ 212 positioned in the 3'-terminal part, the second target nucleic acid-complementary strand 22 positioned at the 5'-terminal side thereof, and the terminal primer B added moiety 232 linked to the 5' end.

As shown in FIG. 4C, the nucleotide sequence $D_2$ 222 in the 3'-terminal part of the amplified fragment 405 and the nucleotide sequence $B_1$ 212 in the 3'-terminal part of the amplified fragment 406 hybridize to each other through further denaturation and annealing. Subsequent extension reaction mediated by polymerase synthesizes the second target nucleic acid 21 originated from the 3' end of the amplified fragment 405 and synthesizes the first target nucleic acid-complementary strand 12 originated from the 3' end of the amplified fragment 406.

As a result of the reaction described above, as shown in FIG. 4D, amplified fragment 407 in which the nucleotide sequence of the first target nucleic acid 11, the nucleotide sequence $D_2$ 222, and the nucleotide sequence of the second target nucleic acid 21 are disposed in this order from the 5' end to the 3' end, and amplified fragment 408 in which the nucleotide sequence of the complementary strand 22 of the second target nucleic acid 21, the nucleotide sequence $B_1$ 212, and the nucleotide sequence of the complementary strand 12 of the first target nucleic acid 11 are disposed in this order from the 5' end to the 3' end hybridize to each other to form, as an amplification product, amplification product 2 containing the amplified fragment 407 linked at its 5' end to the terminal primer A added moiety 202 and the amplified fragment 408 linked at its 5' end to the terminal primer B added moiety 232.

The nucleic acid amplification product 2 is obtained only when both two of the first target nucleic acid 11 (or the first target nucleic acid-complementary strand 12) and the second target nucleic acid 21 (or the second target nucleic acid-complementary strand 22) are present in a template. If one of these target nucleic acids or complementary strands thereof is absent in a template, only the target nucleic acid or the complementary strand thereof present therein is amplified whereas a nucleic acid amplification product having both the binding part and the labeling part is not produced. Thus, negativity is obtained in detection using the labeling part as an index. Hence, the risk of determining false positivity is very low.

The hybridization between the amplified fragment 405 and the amplified fragment 406 shown in FIG. 4C is less likely to proceed in the presence of an excess amount of the first reverse primer 210 or the second forward primer 220 in the reaction system. Therefore, it is preferred for the primer set of this embodiment to perform nucleic acid amplification reaction under conditions involving an increased molar ratio of the terminal primer A 200 and the terminal primer B 230 to the first reverse primer 210 and the second forward primer 220.

The above description is not limited by the case of N=2 and holds true for all the cases where N is 2 or more.

As mentioned above, the nucleic acid amplification reaction using the primer set according to embodiment 2 produces a nucleic acid amplification product comprising:
a first amplified fragment comprising the nucleotide sequence of a first target nucleic acid to the nucleotide sequence of a Nth target nucleic acid in order from the 5' end toward the 3' end; and
a second amplified fragment comprising the nucleotide sequence of a complementary strand of the Nth target nucleic acid to the nucleotide sequence of a complementary strand of the first target nucleic acid in order from the 5' end toward the 3' end, wherein
the first amplified fragment and the second amplified fragment hybridize to each other to from a duplex,
one of the first amplified fragment and the second amplified fragment is linked at its 5' end to the labeling part, and
the other of the first amplified fragment and the second amplified fragment is linked at its 5' end to the binding part.

In this context, N is an integer of 2 or larger. In this nucleic acid amplification product, the first amplified fragment comprises nucleotide sequence $D_{k+1}$ of a (k+1)th forward primer between the nucleotide sequence of a kth target nucleic acid and the nucleotide sequence of a (k+1)th target nucleic acid. The second amplified fragment comprises nucleotide sequence $B_k$ of a kth reverse primer between the nucleotide sequence of a complementary strand of the kth target nucleic acid and the nucleotide sequence of a complementary strand of the (k+1)th target nucleic acid. k is an integer from 1 to N−1.

1.3. Embodiment 3 of Primer Set

Embodiment 3 of the primer set according to one or more embodiments of the present invention relates to a primer set comprising:
terminal primer A comprising a polynucleotide comprising, in its 3'-terminal part, a nucleotide sequence that hybridizes to a 3'-terminal part of a complementary sequence of the nucleotide sequence of a first target nucleic acid;
a kth reverse primer comprising a polynucleotide comprising, in its 3'-terminal part, nucleotide sequence $E_k$ that hybridizes to a 3'-terminal part of the nucleotide sequence of a kth target nucleic acid, and a polynucleotide which is linked at the 5'-terminal side of the polynucleotide comprising the nucleotide sequence $E_k$ and comprises nucleotide sequence $F_k$ that is not double-stranded in nucleic acid amplification reaction;
a (k+1)th forward primer comprising a polynucleotide comprising, in its 3'-terminal part, nucleotide sequence $G_{k+1}$ that hybridizes to a 3'-terminal part of a complementary sequence of the nucleotide sequence of a (k+1)th target nucleic acid, and a polynucleotide which is linked at the 5'-terminal side of the polynucleotide comprising the nucleotide sequence $G_{k+1}$ and comprises nucleotide sequence $H_{k+1}$ that is not double-stranded in nucleic acid amplification reaction, the nucleotide sequence $H_{k+1}$ that hybridizes to the nucleotide sequence $F_k$; and
terminal primer B comprising a polynucleotide comprising, in its 3'-terminal part, a nucleotide sequence that hybridizes to a 3'-terminal part of the nucleotide sequence of a Nth target nucleic acid, wherein
N is an integer of 2 or larger,
k is an integer from 1 to N−1,
the kth reverse primer and the (k+1)th forward primer each involve the case where k is 1 to the case where k is N−1, and
one of the terminal primer A and the terminal primer B further comprises the labeling part, and the other terminal primer further comprises the binding part.

In the primer set of embodiment 3, the terminal primer A and the terminal primer B, the labeling part and the binding part, and structures that link them are the same as in embodiment 1, so that the description will be omitted.

In the kth reverse primer, the nucleotide sequence $E_k$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $E_k$ can comprise the nucleotide sequence $E_k$ in its 3'-terminal part and may further comprise an additional nucleotide sequence upstream from the nucleotide sequence $E_k$. The full length of the polynucleotide comprising the nucleotide sequence $E_k$ is not particularly limited and can be, for example, 40 bases or less, 30 bases or less or 25 bases or less.

In the kth reverse primer, the nucleotide sequence $F_k$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $F_k$ may further comprise an additional nucleotide sequence downstream and/or upstream from the nucleotide sequence $F_k$. The full length of the polynucleotide comprising the nucleotide sequence $F_k$ is not particularly limited and can be, for example, 40 bases or less, 30 bases or less or 25 bases or less.

In the kth reverse primer, the polynucleotide comprising the nucleotide sequence $E_k$ and the polynucleotide comprising the nucleotide sequence $F_k$ are configured so as not to double-strand the latter, together with the former, by extension in nucleic acid amplification reaction. A polynucleotide potentially capable of serving as a template in reaction mediated by DNA polymerase (usually, a polynucleotide consisting of natural nucleotides) may be used as the polynucleotide comprising the nucleotide sequence $F_k$. In this case, the polynucleotide comprising the nucleotide sequence $E_k$ and the polynucleotide comprising the nucleotide sequence $F_k$ are linked to each other via a spacer that inhibits polymerase reaction. The structure already mentioned about the spacer that inhibits polymerase reaction between the polynucleotide and the labeling part or the binding part contained in the terminal primer A or B in embodiment 1 of the primer set can be adopted as such a "spacer". In this case, the polynucleotide comprising the nucleotide sequence $E_k$ and the polynucleotide comprising the nucleotide sequence $F_k$ can be linked in one direction. On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide comprising the nucleotide sequence $F_k$. In this case, the spacer described above that inhibits polymerase reaction may be omitted.

In the (k+1)th forward primer, the nucleotide sequence $G_{k+1}$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $G_{k+1}$ can comprise the nucleotide sequence $G_{k+1}$ in its 3'-terminal part and may further comprise an additional nucleotide sequence upstream from the nucleotide sequence $G_{k+1}$. The full length of the polynucleotide comprising the nucleotide sequence $G_{k+1}$ is not particularly limited and can be, for example, 40 bases or less, 30 bases or less or 25 bases or less.

In the (k+1)th forward primer, the nucleotide sequence $H_{k+1}$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $H_{k+1}$ may further comprise an additional nucleotide sequence downstream and/or upstream from the nucleotide sequence $H_{k+1}$. The full length of the polynucleotide comprising the nucleotide sequence $H_{k+1}$ is not particularly limited and can be, for example, 40 bases or less, 30 bases or less or 25 bases or less.

In the (k+1)th forward primer, the polynucleotide comprising the nucleotide sequence $G_{k+1}$ and the polynucleotide comprising the nucleotide sequence $H_{k+1}$ are configured so as not to double-strand the latter, together with the former, by extension in nucleic acid amplification reaction. A polynucleotide potentially capable of serving as a template in reaction mediated by DNA polymerase (usually, a polynucleotide consisting of natural nucleotides) may be used as the polynucleotide comprising the nucleotide sequence $H_{k+1}$. In this case, the polynucleotide comprising the nucleotide sequence $G_{k+1}$ and the polynucleotide comprising the nucleotide sequence $H_{k+1}$ are linked to each other via a spacer that inhibits polymerase reaction. The structure already mentioned about the spacer that inhibits polymerase reaction between the polynucleotide and the labeling part or the binding part contained in the terminal primer A or B in embodiment 1 of the primer set can be adopted as such a "spacer". In this case, the polynucleotide comprising the nucleotide sequence $G_{k+1}$ and the polynucleotide comprising the nucleotide sequence $H_{k+1}$ can be linked in one direction. On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide comprising the nucleotide sequence $H_{k+1}$. In this case, the spacer described above that inhibits polymerase reaction may be omitted.

The nucleotide sequence $F_k$ of the kth reverse primer and the nucleotide sequence $H_{k+1}$ of the (k+1)th forward primer can be appropriately designed so as to hybridize mutually and not to inhibit nucleic acid amplification with each primer contained in the primer set.

The case of using first target nucleic acid 11 and second target nucleic acid 21 as two target nucleic acids (i.e., N=2) will be taken as an example, and the function of the primer set of embodiment 3 will be described with reference to FIG. 5.

Terminal primer A 500 comprises polynucleotide 501 comprising, in its 3'-terminal part, a nucleotide sequence that hybridizes to a 3'-terminal part of the nucleotide sequence of complementary strand 12 of the first target nucleic acid 11. The terminal primer A 500 further has terminal primer A added moiety 502 in addition to the polynucleotide 501. The terminal primer A added moiety 502 is any one of the labeling part and the binding part.

The example of FIG. 5 involves first reverse primer 510 as the kth reverse primer and involves second forward primer 520 as the (k+1)th forward primer because of N=2.

The first reverse primer 510 comprises polynucleotide 511 comprising, in its 3'-terminal part, nucleotide sequence $E_1$ that hybridizes to a 3'-terminal part of the nucleotide sequence of the first target nucleic acid, and polynucleotide 512 which is linked at the 5'-terminal side of the polynucleotide 511 comprising the nucleotide sequence $E_1$ and comprises nucleotide sequence $F_1$.

The second forward primer 520 comprises polynucleotide 521 comprising, in its 3'-terminal part, nucleotide sequence $G_2$ that hybridizes to a 3'-terminal part of complementary sequence 22 of the nucleotide sequence of the second target nucleic acid 21, and polynucleotide 522 which is linked at the 5'-terminal side of the polynucleotide 521 comprising the nucleotide sequence $G_2$ and comprises nucleotide sequence $H_2$ that hybridizes to the nucleotide sequence $F_1$.

Terminal primer B 530 comprises polynucleotide 531 comprising, in its 3'-terminal part, a nucleotide sequence that hybridizes to a 3'-terminal part of the nucleotide sequence of the second target nucleic acid 21. The terminal primer B 530 further has terminal primer B added moiety 532 in addition to the polynucleotide 531. The terminal primer B added moiety 532 is any one of the labeling part and the binding part.

As shown in FIG. 5A, nucleic acid amplification reaction is performed using the nucleic acids as a template in the presence of the primer set of the embodiment 3 comprising the terminal primer A 500, the first reverse primer 510, the second forward primer 520 and the terminal primer B 530. In this reaction, the polynucleotide 501 of the terminal primer A 500 hybridizes to the 3'-terminal part of the first target nucleic acid-complementary strand 12 through denaturation and annealing. Extension reaction mediated by polymerase synthesizes amplified fragment 551 of the first target nucleic acid 11 linked at its 5' end to the terminal primer A added moiety 502.

Likewise, as shown in FIG. 5A, the polynucleotide 511 comprising the nucleotide sequence $E_1$ in the first reverse primer 510 hybridizes to the 3'-terminal part of the first target nucleic acid 11 through denaturation and annealing. Extension reaction mediated by polymerase synthesizes amplified fragment 552 of the first target nucleic acid-complementary strand 12 linked at its 5'-terminal side to the polynucleotide 512 comprising the nucleotide sequence $F_1$.

Likewise, as shown in FIG. 5A, the polynucleotide 521 comprising the nucleotide sequence $G_2$ in the second forward primer 520 hybridizes to the 3'-terminal part of the second target nucleic acid-complementary strand 22 through denaturation and annealing. Extension reaction mediated by polymerase synthesizes amplified fragment 553 of the second target nucleic acid 21 linked at its 5'-terminal side to the polynucleotide 522 comprising the nucleotide sequence $H_2$.

Likewise, as shown in FIG. 5A, the polynucleotide 531 of the terminal primer B 530 hybridizes to the 3'-terminal part of the second target nucleic acid 21 through denaturation and annealing. Extension reaction mediated by polymerase synthesizes amplified fragment 554 of the second target nucleic acid-complementary strand 22 linked at its 5' end to the terminal primer B added moiety 532.

As shown in FIG. 5B, further denaturation and annealing produces nucleic acid amplification product 3 in which the moiety of the first target nucleic acid 11 of the amplified fragment 551 and the moiety of the first target nucleic acid-complementary strand 12 of the amplified fragment 552 are hybridized to each other, the moiety of the polynucleotide 512 comprising the nucleotide sequence $F_1$ in the amplified fragment 552 and the moiety of the polynucleotide 522 comprising the nucleotide sequence $H_2$ in the amplified fragment 553 are hybridized to each other, and the moiety of the second target nucleic acid 21 of the amplified fragment 553 and the moiety of the second target nucleic acid-complementary strand 22 of the amplified fragment 554 are hybridized to each other.

The nucleic acid amplification product 3 is obtained only when both two of the first target nucleic acid 11 (or the first target nucleic acid-complementary strand 12) and the second target nucleic acid 21 (or the second target nucleic acid-complementary strand 22) are present in a template. If one of these target nucleic acids or complementary strands thereof is absent in a template, only the target nucleic acid or the complementary strand thereof present therein is amplified whereas a nucleic acid amplification product having both the binding part and the labeling part is not produced. Thus, negativity is obtained in detection using the labeling part as an index. Hence, the risk of determining false positivity is very low.

The hybridization among the amplified fragments 551 to 554 shown in FIG. 5B is less likely to proceed in the presence of an excess amount of the first reverse primer 510 or the second forward primer 520 in the reaction system. Therefore, it is preferred for the primer set of this embodiment to perform nucleic acid amplification reaction under conditions involving an increased molar ratio of the terminal primer A 500 and the terminal primer B 530 to the first reverse primer 510 and the second forward primer 520.

The above description is not limited by the case of N=2 and holds true for all the cases where N is 2 or more.

As mentioned above, the nucleic acid amplification reaction using the primer set according to embodiment 3 produces a nucleic acid amplification product comprising double-stranded amplified fragments of target nucleic acids from a first target nucleic acid to a Nth target nucleic acid hybridized to their respective complementary strands, wherein a single-stranded polypeptide is linked at the 5'-terminal side of each of the target nucleic acids from the second target nucleic acid to the Nth target nucleic acid, a single-stranded polypeptide is linked at the 5'-terminal side of each of complementary strands of the target nucleic acids from the first target nucleic acid to the (N−1)th target nucleic acid, the single-stranded polypeptide linked at the 5'-terminal side of a complementary strand of a kth target nucleic acid in the double-stranded amplified fragment of the kth target nucleic acid and the single-stranded polypeptide linked at the 5'-terminal side of a (k+1)th target nucleic acid in the double-stranded amplified fragment of the (k+1)th target nucleic acid are hybridized to each other, one of the amplified fragment of the first target nucleic acid and the amplified fragment of the complementary strand of the Nth target nucleic acid is linked at its 5' end to the labeling part, and the other of the amplified fragment of the first target nucleic acid and the amplified fragment of the complementary strand of the Nth target nucleic acid is linked at its 5' end to the binding part.

In this context, N is an integer of 2 or larger, and k is an integer of 1 to N−1.

1.4. Embodiment 4

Embodiment 4 of the primer set according to one or more embodiments of the present invention relates to a primer set comprising:

terminal primer A comprising a polynucleotide comprising, in its 3'-terminal part, a nucleotide sequence that hybridizes to a 3'-terminal part of a complementary sequence of the nucleotide sequence of a first target nucleic acid;

a kth reverse primer comprising a polynucleotide comprising, in its 3'-terminal part, nucleotide sequence $I_k$ that hybridizes to a 3'-terminal part of the nucleotide sequence of a kth target nucleic acid, and a polynucleotide which is linked at the 5'-terminal side of the polynucleotide comprising the nucleotide sequence $I_k$ and comprises nucleotide sequence $J_k$ that is not double-stranded in nucleic acid amplification reaction;

a (k+1)th forward primer comprising a polynucleotide comprising, in its 3'-terminal part, nucleotide sequence $L_{k+1}$ that hybridizes to a 3'-terminal part of a complementary sequence of the nucleotide sequence of a (k+1)th target nucleic acid, and a polynucleotide which is linked at the 5'-terminal side of the nucleotide sequence $L_{k+1}$ and further comprises nucleotide sequence $M_{k+1}$ that is not double-stranded in nucleic acid amplification reaction;

a kth linking polynucleotide comprising a polynucleotide comprising a nucleotide sequence that hybridizes to the nucleotide sequence $J_k$, and a polynucleotide comprising a nucleotide sequence that hybridizes to the nucleotide sequence $M_{k+1}$; and terminal primer B comprising a polynucleotide comprising, in its 3'-terminal part, a nucleotide sequence that hybridizes to a 3'-terminal part of the nucleotide sequence of a Nth target nucleic acid, wherein N is an integer of 2 or larger, k is an integer from 1 to N−1, the kth reverse primer, the (k+1)th forward primer and the kth linking polynucleotide each involve the case where k is 1 to the case where k is N−1, and one of the terminal primer A and the terminal primer B further comprises the labeling part, and the other terminal primer further comprises the binding part.

In the primer set of embodiment 4, the terminal primer A and the terminal primer B, the labeling part and the binding part, and structures that link them are the same as in embodiment 1, so that the description will be omitted.

In the kth reverse primer of embodiment 4, the nucleotide sequence $I_k$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $I_k$ can comprise the nucleotide sequence $I_k$ in its 3'-terminal part and may further comprise an additional nucleotide sequence upstream from the nucleotide sequence $I_k$. The full length of the polynucleotide comprising the nucleotide sequence $I_k$ is not particularly limited and can be, for example, 40 bases or less, 30 bases or less or 25 bases or less.

In the kth reverse primer, the nucleotide sequence $J_k$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $J_k$ may further comprise an additional nucleotide sequence downstream and/or upstream from the nucleotide sequence $J_k$. The full length of the polynucleotide comprising the nucleotide sequence $J_k$ is not particularly limited and can be, for example, 40 bases or less, 30 bases or less or 25 bases or less.

In the kth reverse primer, the polynucleotide comprising the nucleotide sequence $I_k$ and the polynucleotide comprising the nucleotide sequence $J_k$ are configured so as not to double-strand the latter, together with the former, by extension in nucleic acid amplification reaction. A polynucleotide potentially capable of serving as a template in reaction mediated by DNA polymerase (usually, a polynucleotide consisting of natural nucleotides) may be used as the polynucleotide comprising the nucleotide sequence $J_k$. In this case, the polynucleotide comprising the nucleotide sequence $I_k$ and the polynucleotide comprising the nucleotide sequence $J_k$ are linked to each other via a spacer that inhibits polymerase reaction. The structure already mentioned about the spacer that inhibits polymerase reaction between the polynucleotide and the labeling part or the binding part contained in the terminal primer A or B in embodiment 1 of the primer set can be adopted as such a "spacer". In this case, the polynucleotide comprising the nucleotide sequence $I_k$ and the polynucleotide comprising the nucleotide sequence $J_k$ can be linked in one direction. On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide comprising the nucleotide sequence $J_k$. In this case, the spacer described above that inhibits polymerase reaction may be omitted.

In the (k+1)th forward primer, the nucleotide sequence $L_{k+1}$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $L_{k+1}$ can comprise the nucleotide sequence $L_{k+1}$ in its 3'-terminal part and may further comprise an additional nucleotide sequence upstream from the nucleotide sequence $L_{k+1}$. The full length of the polynucleotide comprising the nucleotide sequence $L_{k+1}$ is not particularly limited and can be, for example, 40 bases or less, 30 bases or less or 25 bases or less.

In the (k+1)th forward primer, the nucleotide sequence $M_{k+1}$ is not particularly limited by its length. The length can be, for example, 8 bases or more, 12 bases or more, or 15 bases or more and can be 40 bases or less, 30 bases or less, or 25 bases or less. The polynucleotide comprising the nucleotide sequence $M_{k+1}$ may further comprise an additional nucleotide sequence downstream and/or upstream from the nucleotide sequence $M_{k+1}$. The full length of the polynucleotide comprising the nucleotide sequence $M_{k+1}$ is not particularly limited and can be, for example, 40 bases or less, 30 bases or less or 25 bases or less.

In the (k+1)th forward primer, the polynucleotide comprising the nucleotide sequence $L_{k+1}$ and the polynucleotide comprising the nucleotide sequence $M_{k+1}$ are configured so as not to double-strand the latter, together with the former, by extension in nucleic acid amplification reaction. A polynucleotide potentially capable of serving as a template in reaction mediated by DNA polymerase (usually, a polynucleotide consisting of natural nucleotides) may be used as the polynucleotide comprising the nucleotide sequence $M_{k+1}$. In this case, the polynucleotide comprising the nucleotide sequence $L_{k+1}$ and the polynucleotide comprising the nucleotide sequence $M_{k+1}$ are linked to each other via a spacer that inhibits polymerase reaction. The structure already mentioned about the spacer that inhibits polymerase reaction between the polynucleotide and the labeling part or the binding part contained in the terminal primer A or B in embodiment 1 of the primer set can be adopted as such a "spacer". In this case, the polynucleotide comprising the nucleotide sequence $L_{k+1}$ and the polynucleotide comprising the nucleotide sequence $M_{k+1}$ can be linked in one direction. On the other hand, a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide) may be used as the polynucleotide comprising the nucleotide sequence $M_{k+1}$. In this case, the spacer described above that inhibits polymerase reaction may be omitted.

In the kth linking polynucleotide, the polynucleotide comprising a nucleotide sequence that hybridizes to the nucleotide sequence $J_k$ may further comprise an additional nucleotide sequence at the 5'-terminal and/or 3'-terminal side of the nucleotide sequence that hybridizes to the nucleotide sequence $J_k$.

In the kth linking polynucleotide, the polynucleotide comprising a nucleotide sequence that hybridizes to the nucleotide sequence $M_{k+1}$ may further comprise an additional nucleotide sequence at the 5'-terminal and/or 3'-terminal side of the nucleotide sequence that hybridizes to the nucleotide sequence $M_{k+1}$.

The polynucleotide comprising a nucleotide sequence that hybridizes to the nucleotide sequence $J_k$ and the polynucleotide comprising a nucleotide sequence that hybridizes to the nucleotide sequence $M_{k+1}$, contained in the kth linking polynucleotide may be one polynucleotide molecule without mediation or may be linked via an appropriate chemical structure that intervenes therebetween. For example, the structure already mentioned about the structure between the polynucleotide and the labeling part or the binding part contained in the terminal primer A or B in embodiment 1 of the primer set can be adopted as such a chemical structure. Preferably, the kth linking polynucleotide has a structure that does not serve as a template in reaction mediated by DNA polymerase. For example, the polynucleotide comprising a nucleotide sequence that hybridizes to the nucleotide sequence $J_k$ and the polynucleotide comprising a nucleotide sequence that hybridizes to the nucleotide sequence $M_{k+1}$ may be linked to each other at their 3'-terminal sides. Alternatively, one or both of the polynucleotide comprising a nucleotide sequence that hybridizes to the nucleotide sequence $J_k$ and the polynucleotide comprising a nucleotide sequence that hybridizes to the nucleotide sequence $M_{k+1}$ may be constituted by a polynucleotide that neither serves as a template in reaction mediated by DNA polymerase nor is double-stranded by extension in nucleic acid amplification reaction (such as, for example, a polynucleotide containing a modified nucleic acid such as LNA (locked nucleic acid), a nucleic acid in a L form, or a 2'-O-methylated nucleotide).

The nucleotide sequence $J_k$ of the kth reverse primer, the nucleotide sequence $M_{k+1}$ of the (k+1)th forward primer, and the nucleotide sequences that hybridize to these nucleotide sequences, contained in the kth linking polynucleotide can be appropriately designed so as not to inhibit nucleic acid amplification with each primer contained in the primer set.

The case of using first target nucleic acid 11 and second target nucleic acid 21 as two target nucleic acids (i.e., N=2) will be taken as an example, and the function of the primer set of embodiment 4 will be described with reference to FIG. 6.

Terminal primer A 600 has polynucleotide 601 comprising, in its 3'-terminal part, a nucleotide sequence that hybridizes to a 3'-terminal part of the nucleotide sequence of complementary strand 12 of the first target nucleic acid 11, and terminal primer A added moiety 602.

The example of FIG. 6 involves first reverse primer 610 as the kth reverse primer, involves second forward primer 620 as the (k+1)th forward primer, and involves first linking polynucleotide 640 as the kth linking polynucleotide because of N=2.

The first reverse primer 610 comprises polynucleotide 611 comprising nucleotide sequence $I_1$ in its 3'-terminal part and polynucleotide 612 which is linked at the 5'-terminal side of the polynucleotide 611 and comprises nucleotide sequence Ji.

The second forward primer 620 comprises polynucleotide 621 comprising nucleotide sequence $L_2$ in its 3'-terminal part and polynucleotide 622 which is linked at the 5'-terminal side of the polynucleotide 621 and comprises nucleotide sequence $M_2$.

Terminal primer B 630 has polynucleotide 631 comprising, in its 3'-terminal part, a nucleotide sequence that hybridizes to a 3'-terminal part of the nucleotide sequence of the second target nucleic acid 21, and terminal primer B added moiety 632.

The first linking polynucleotide 640 comprises polynucleotide 641 comprising a nucleotide sequence that hybridizes to the polynucleotide 612 comprising the nucleotide sequence Ji, and polynucleotide 642 comprising a nucleotide sequence that hybridizes to the polynucleotide 622 comprising the nucleotide sequence $M_2$.

As shown in FIG. 6A, nucleic acid amplification reaction is performed using the nucleic acids as a template in the presence of the primer set of the embodiment 4 comprising the terminal primer A 600, the first reverse primer 610, the second forward primer 620 and the terminal primer B 630. In this reaction, amplified fragment 651 of the first target nucleic acid 11 linked at its 5' end to the terminal primer A added moiety 602 is synthesized from the terminal primer A 600.

Amplified fragment 652 of the first target nucleic acid-complementary strand 12 linked at its 5'-terminal side to the polynucleotide 612 comprising the nucleotide sequence Ji is synthesized from the first reverse primer 610.

Amplified fragment 653 of the second target nucleic acid 21 linked at its 5'-terminal side to the polynucleotide 622 comprising the nucleotide sequence $M_2$ is synthesized from the second forward primer 620.

Amplified fragment 654 of the second target nucleic acid-complementary strand 22 linked at its 5' end to the terminal primer B added moiety 632 is synthesized from the terminal primer B 630.

The first linking polynucleotide 640 is not directly involved in the nucleic acid amplification reaction.

As shown in FIG. 5B, the denaturation and annealing of the amplification product after the nucleic acid amplification reaction produces nucleic acid amplification product 4 in which the moiety of the first target nucleic acid 11 of the amplified fragment 651 and the moiety of the first target nucleic acid-complementary strand 12 of the amplified fragment 652 are hybridized to each other, the moiety of the polynucleotide 612 of the amplified fragment 652 and the moiety of the polypeptide 641 of the first linking polynucleotide 640 are hybridized to each other, the moiety of the polypeptide 642 of the first linking polynucleotide 640 and the moiety of the polynucleotide 622 of the amplified fragment 653 are hybridized to each other, and the moiety of the second target nucleic acid 21 of the amplified fragment 653 and the moiety of the second target nucleic acid-complementary strand 22 of the amplified fragment 654 are hybridized to each other.

The nucleic acid amplification product 4 is obtained only when both two of the first target nucleic acid 11 (or the first target nucleic acid-complementary strand 12) and the second target nucleic acid 21 (or the second target nucleic acid-complementary strand 22) are present in a template. If one of these target nucleic acids or complementary strands thereof is absent in a template, only the target nucleic acid or the complementary strand thereof present therein is amplified whereas a nucleic acid amplification product having both the binding part and the labeling part is not produced. Thus, negativity is obtained in detection using the labeling part as an index. Hence, the risk of determining false positivity is very low.

The hybridization among the amplified fragments 651 to 654 and the first linking polynucleotide 640 shown in FIG. 6B is less likely to proceed in the presence of an excess amount of the first reverse primer 610 or the second forward primer 620 in the reaction system. Therefore, it is preferred for the primer set of this embodiment to perform nucleic acid amplification reaction under conditions involving an increased molar ratio of the terminal primer A 600 and the terminal primer B 630 to the first reverse primer 610 and the second forward primer 620.

The kth linking polynucleotide is not directly involved in the nucleic acid amplification reaction and may therefore be added into the reaction system after the nucleic acid amplification reaction, followed by the denaturation and annealing of the reaction system.

The above description is not limited by the case of N=2 and holds true for all the cases where N is 2 or more.

As mentioned above, the nucleic acid amplification reaction using the primer set according to embodiment 4 according to one or more embodiments of the present invention produces a nucleic acid amplification product comprising:

double-stranded amplified fragments of target nucleic acids from a first target nucleic acid to a Nth target nucleic acid hybridized to their respective complementary strands; and N−1 linking polynucleotide(s) from a first linking polynucleotide to a (N−1)th linking polynucleotide, wherein a single-stranded polypeptide is linked at the 5'-terminal side of each of the target nucleic acids from the second target nucleic acid to the Nth target nucleic acid, a single-stranded polypeptide is linked at the 5'-terminal side of each of complementary strands of the target nucleic acids from the first target nucleic acid to the (N−1)th target nucleic acid, the single-stranded polypeptide linked at the 5'-terminal side of a complementary strand of a kth target nucleic acid and a portion of a kth linking polynucleotide are hybridized to each other, the single-stranded polypeptide linked at the 5'-terminal side of a (k+1)th target nucleic acid and another portion of the kth linking polynucleotide are hybridized to each other, one of the amplified fragment of the first target nucleic acid and the amplified fragment of the complementary strand of the Nth target nucleic acid is linked at its 5' end to the labeling part, and the other of the amplified fragment of the first target nucleic acid and the amplified fragment of the complementary strand of the Nth target nucleic acid is linked at its 5' end to the binding part.

In this context, N is an integer of 2 or larger, and k is an integer of 1 to N−1.

<2. Detection Method>

One or more embodiments of the present invention also relate to a method for detecting two or more target nucleic acids, the method comprising a detection step of contacting a sample for detection possibly comprising a nucleic acid for detection comprising the two or more target nucleic acids, a labeling part which is a labeling agent or is a tag capable of binding to a labeling agent, and a binding part which is a tag capable of binding to a solid-phase support, linked to each other, with a solid-phase support at least partially comprising a moiety capable of binding to the binding part, and detecting the nucleic acid for detection at the moiety of the solid-phase support with the labeling part as an index.

As described on the basis of FIG. 2, a mixture of two or more target nucleic acids each bound with a binding part and a labeling part is contacted with one solid-phase support containing a plurality of binding sites according to each binding part. The problem of this approach is poor identification performance.

In one or more embodiments of the present invention, a nucleic acid comprising the two or more target nucleic acids, the labeling part, and the binding part linked to each other is used as a nucleic acid for detection. A sample for detection possibly comprising the nucleic acid for detection is contacted with a solid-phase support at least partially comprising a moiety capable of binding to the binding part. The nucleic acid for detection at the moiety of the solid-phase support is detected with the labeling part as an index. The nucleic acid for detection at the moiety of the solid-phase support can be detected on the basis of the presence or absence of the labeling part at the moiety. As shown in FIG. 1A, when the nucleic acid for detection is detected at the moiety of the solid-phase support, it can be determined that the predetermined two or more target nucleic acids are contained in the sample for detection. Therefore, the identification performance is much higher than that of the method which involves contacting a mixture of two or more target nucleic acids each bound with a binding part and a labeling part with one solid-phase support containing a plurality of binding sites according to each binding part.

In one or more embodiments of the present invention, two or more target nucleic acids are included in one nucleic acid for detection. Hence, one site binding to the binding part can be disposed on a solid-phase support. Thus, another advantage is that the configuration of the solid-phase support can be simplified.

In this context, the nucleic acid for detection preferably comprises two or more target nucleic acids linked in series, the labeling part linked at one of both ends of the line of the two or more target nucleic acids, and the binding part linked at the other end. In this case, the labeling part and the binding part can coexist in one nucleic acid only when all the predetermined two or more target sequences are contained therein. As shown in FIGS. 1B to 1D, if the two or more target nucleic acids are absent, the label ascribable to the labeling part is not detected on the solid-phase support. Hence, the risk of false positivity can be reduced.

The detection method according to one or more embodiments of the present invention is more preferably the method for detecting two or more target nucleic acids, further comprising a sample-for-detection preparation step of preparing the sample for detection possibly comprising the nucleic acid for detection by nucleic acid amplification reaction using a nucleic acid obtained from a sample to be analyzed as a template, wherein in the detection step, a product of the nucleic acid amplification reaction obtained in the sample-for-detection preparation step is used as the sample for detection.

In the detection step, the nucleic acid for detection is a nucleic acid amplification product of the nucleic acid amplification reaction.

In the detection method according to one or more embodiments of the present invention, more preferably, the sample-for-detection preparation step comprises performing nucleic acid amplification reaction using a nucleic acid obtained from a sample to be analyzed as a template and a primer set according to one or more embodiments of the present invention. By use of the primer set according to one or more embodiments of the present invention, the nucleic acid for detection comprising target nucleic acids from a first target nucleic acid to a Nth target nucleic acid linked in series, the labeling part linked at one of both ends of the line of the two or more target nucleic acids, and the binding part linked at the other end can be obtained as a nucleic acid amplification product when all of the first target nucleic acid to the Nth target nucleic acid are contained in the nucleic acid serving as a template. On the other hand, if one or more of the target nucleic acids are absent, the product of the nucleic acid amplification reaction neither comprises the nucleic acid for detection nor comprises a nucleic acid species comprising both the labeling part and the binding part. For example, as shown in FIGS. 1B to 1D, if one or two of target nucleic acid A, target nucleic acid B, and target nucleic acid C are absent, the label ascribable to the labeling part is not detected on the solid-phase support. Hence, the risk of false positivity can be reduced.

In one or more embodiments of the present invention, examples of the sample to be analyzed typically include, but are not particularly limited to, samples containing food or drink, a portion (organs, tissues, cells, blood, body fluids, etc.) of organisms such as animals and plants, feces, microbes, viruses or the like.

A nucleic acid obtained from the sample to be analyzed can be used as a template in nucleic acid amplification reaction. The nucleic acid may be in a form extracted from the sample to be analyzed and purified, or may be in a form extracted from the sample to be analyzed and partially purified. Alternatively, a sample containing the nucleic acid at a relatively high concentration, such as a portion of a cell or a tissue may be directly involved as the sample to be analyzed itself in nucleic acid amplification reaction. Also, cDNA prepared from the sample to be analyzed is available as a template. The nucleic acid for use as a template is preferably DNA.

Hereinafter, preferred embodiments of the sample-for-detection preparation step, the detection step, and a labeling step will be described.

(2.1. Sample-for-Detection Preparation Step)

A preferred aspect of the sample-for-detection preparation step of performing nucleic acid amplification reaction using a nucleic acid obtained from a sample to be analyzed as a template and the primer set according to one or more embodiments of the present invention mentioned above will be described below.

The nucleic acid amplification reaction can be performed in accordance with polymerase chain reaction (PCR). Specifically, PCR using the primer set according to one or more embodiments of the present invention for a template nucleic acid containing target nucleic acids can be performed under PCR conditions that yield the desired nucleic acid amplification product. Alternatively, nucleic acid amplification reaction other than PCR may be used, if appropriate.

The DNA polymerase for use in PCR can be any thermostable DNA polymerase and is not particularly limited. In one or more embodiments of the present invention, commercially available DNA polymerase can be used. For example, TaKaRa Ex Taq(R) can be suitably used. Temperature, time, the composition of a buffer solution, etc. can be appropriately selected according to the DNA polymerase used, the concentration of each primer, etc.

Hot start PCR is useful because this method can be expected to be effective for suppressing primer dimer formation. The hot start PCR can be performed using a commercially available reagent for hot start PCR, such as TaKaRa Ex Taq(R) Hot Start Version (Takara Bio Inc.). Also, TaKaRa Taq HS PCR Kit, UNG plus(R) may be used. Use of this kit can be expected to be also effective for suppressing carry-over contamination of a nucleic acid amplification product.

Each condition, such as time, temperature, buffer solution composition, dNTP concentration, or the number of cycles, for each step of denaturation, annealing, and extension in PCR can be appropriately set in consideration of factors such as the selected DNA polymerase, the primer sequences, the numbers of bases in the target nucleic acids, and template concentration.

The number of cycles in PCR is not particularly limited and is within the range of, for example, 25 to 60 cycles.

Each primer concentration in the reaction system at the start of PCR is not particularly limited and can be appropriately adjusted according to the amount of the nucleic acid serving as a template, etc. Preferred examples of the primer concentration in the reaction system at the start of reaction include concentrations of 0.05 µM or higher and 1.0 µM or lower of each primer. A primer concentration of lower than 0.05 µM might reduce detection sensitivity, causing reduction in reference detection sensitivity. The upper limit of the primer concentration is not particularly limited and is preferably 1.0 µM.

In nucleic acid amplification reactions using the primer sets of embodiments 1 to 4, the nucleic acid amplification products 1 to 4 described above are formed as amplification products in the reaction systems when the target nucleic acids are present in the template nucleic acids.

In the case of detecting two or more combinations of two or more target nucleic acids, nucleic acid amplification reaction can be performed under the conditions described above using two or more primer sets according to one or more embodiments of the present invention and a nucleic acid obtained from a sample to be analyzed as a template, wherein the two or more primer sets are designed so as to be able to produce two or more nucleic acids for detection each comprising a different combination of the two or more target nucleic acids and each having the binding part capable of binding to a distinct position of the solid-phase support. In this case, the detection step described below involves contacting the sample for detection obtained in the nucleic acid amplification reaction with the solid-phase support, and detecting each of the two or more nucleic acids for detection in the solid-phase support with the labeling part as an index.

(2.2. Detection Step)

The detection step is the step of contacting a sample for detection such as a product of nucleic acid amplification reaction in the sample-for-detection preparation step with a solid-phase support at least partially comprising a moiety capable of binding to the binding part, and detecting the nucleic acid for detection at the moiety of the solid-phase support with the labeling part as an index.

The product of nucleic acid amplification reaction refers to, for example, a reaction solution for nucleic acid amplification reaction possibly containing the nucleic acid for detection as an amplification product, or a sample prepared from the reaction solution so as to have a increased concentration of the amplification product.

When the labeling part is the tag for labeling mentioned above, a labeling step of binding a labeling agent to the tag for labeling can be further performed. When the labeling part is the labeling agent mentioned above, the labeling step is unnecessary. In the detection step, the phrase "with the labeling part as an index" means that, when the labeling part is the tag for labeling, the nucleic acid for detection is detected by using the labeling agent bound through the labeling step as an index, and means that, when the labeling part is the labeling agent, the nucleic acid for detection is detected by using the labeling agent as an index.

The solid-phase support is as already mentioned in detail.

The contact of the sample for detection with the moiety capable of binding to the binding part, in the solid-phase support can be performed according to the combination of the solid-phase support and the binding part under conditions appropriately adjusted (e.g., the hybridization conditions mentioned in detail about the binding part, or buffer solution conditions on the order of pH 5 to 9) such that the binding part of the nucleic acid for detection binds to the moiety when the nucleic acid for detection is contained in the sample for detection.

The detection of the nucleic acid for detection can be performed by detecting, preferably visually detecting the labeling agent bound with the nucleic acid for detection captured on the solid-phase support. The labeling agent of the nucleic acid for detection captured and bound on the solid-phase support is detected in the presence of the nucleic acid for detection. The presence or absence of the nucleic acid for detection in the sample for detection can be identified with the presence or absence of the detection as an index. When the sample for detection is a product of nucleic acid amplification reaction in the sample-for-detection preparation step, the presence or absence of the two or more target nucleic acids in the sample to be analyzed can be identified with the presence or absence of the detection as an index.

(2.3. Labeling Step)

The labeling step is a step that is performed when the labeling part contained in the nucleic acid for detection is the tag for labeling mentioned above. This step is performed by contacting the sample for detection with a labeling agent to bind the labeling agent to the tag for labeling. The labeling step may be performed before the contact of the sample for detection with the solid-phase support, may be performed after the contact, or may be performed at the same time with the contact.

The contact of the sample for detection with the labeling agent can be performed according to the combination of the labeling agent and the tag for labeling under conditions appropriately adjusted (e.g., the hybridization conditions described about the binding part, or buffer solution conditions on the order of pH 5 to 9) such that the labeling agent binds to the tag for labeling in the sample for detection when the target nucleic acids are contained in the sample for detection.

<3. Kit>

One or more embodiments of the present invention also provide a kit for detecting two or more target nucleic acids in a sample to be analyzed, the kit comprising: the primer set according to one or more embodiments of the present invention; and a solid-phase support at least partially comprising a moiety capable of binding to the binding part. The kit can be used in the detection method according to one or more embodiments of the present invention.

When the labeling part in the primer set according to one or more embodiments of the present invention is the tag for labeling, the kit according to one or more embodiments of the present invention can further comprise a labeling agent.

The solid-phase support and the labeling agent can be in the form of a nucleic acid detection device mentioned later.

The kit according to one or more embodiments of the present invention can further comprise a buffer solution for PCR, dNTPs, DNA polymerase, a nucleic acid chromatography developing solution, and the like.

<4. Nucleic Acid Detection Device>

The detection step and the labeling step mentioned above can be performed using a nucleic acid detection device through the use of nucleic acid chromatography. By use of the nucleic acid detection device, the presence or absence of the nucleic acid for detection in the sample for detection can be detected and identified without the need of a special apparatus, and results can be obtained conveniently and rapidly.

The nucleic acid detection device can employ a known nucleic acid detection device (WO2012/070618) that is used for detecting the labeled nucleic acid for detection by nucleic acid chromatography.

Figure 7:
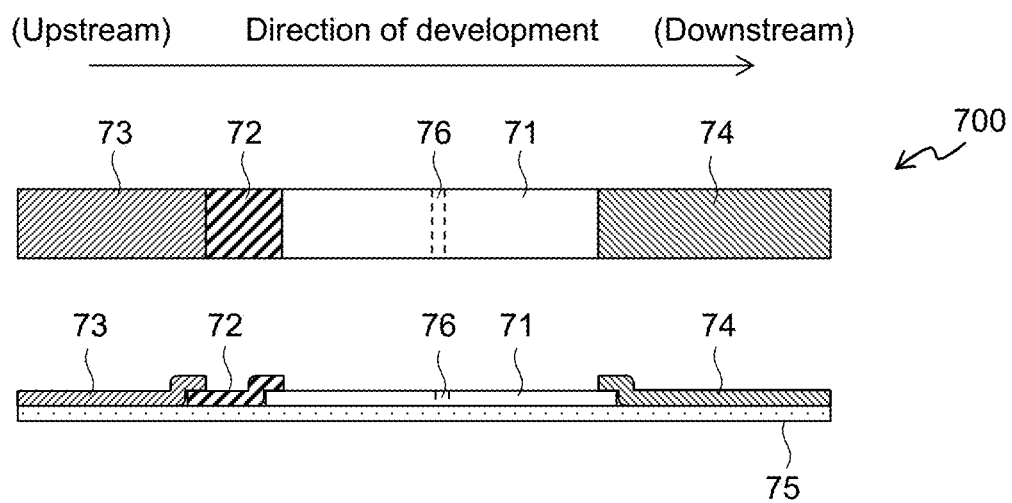
FIG. 7 shows schematic diagrams of lateral flow-type nucleic acid detection device 700. Reference numeral 71 denotes a solid-phase support, reference numeral 72 denotes a conjugate pad (labeling agent retention part), reference numeral 73 denotes a sample pad (reaction system reception part), reference numeral 74 denotes an absorption pad, reference numeral 75 denotes a substrate, and reference numeral 76 denotes a moiety containing a tag capture unit of the solid-phase support 71.

FIG. 7 shows a schematic diagram of one embodiment of the nucleic acid detection device available in one or more embodiments of the present invention. However, the nucleic acid detection device is not limited by this embodiment. In the description below, a reference numeral on each member corresponds to the reference numeral in FIG. 7.

Nucleic acid detection device 700 of FIG. 7 is formed by disposing, on substrate 75, sample pad 73 which is a reaction system reception part for receiving the sample for detection, conjugate pad 72 which retains a labeling agent, porous solid-phase support 71 partially comprising moiety 76 capable of binding to the binding part contained in the nucleic acid for detection, and absorption pad 74, in contact with each other in this order. The moiety 76 of the solid-phase support 71 is a moiety in which a unit for capturing the nucleic acid for detection (capture unit) (e.g., the oligonucleotide described above) is disposed and immobilized in a localized manner. The sample pad 73, the conjugate pad 72, the solid-phase support 71 and the absorption pad 74 can each be constituted by a member having a porous structure available as the solid-phase support described above. These components may be constituted by the same member or may be constituted by different members. The substrate 75 can be any substrate that can support various members disposed thereon and facilitates the operation of the nucleic acid detection device. For example, a substrate made of a resin, a metal, a mineral, or the like can be used. When the labeling agent is mixed into a developing solution or when the labeling part is the labeling agent, the conjugate pad 72 can be omitted. The nucleic acid detection device 700 may be partially covered with a polyester film or the like in order to prevent contamination or prevent liquid volatilization from solid-phase support surface during tests.

The sample for detection such as a reaction system of nucleic acid amplification reaction obtained by the nucleic acid amplification step is added to the sample pad 73. The reaction system may be added directly as the sample for detection or may be added together with an appropriate developing solution (e.g., a phosphate buffer solution, a Tris buffer solution, a Good's buffer solution, or a SSC buffer solution). The developing solution can further contain, if necessary, a surfactant, a salt, a protein, a nucleic acid, or the like. The sample for detection added to the sample pad 73 develops by a capillary phenomenon from upstream toward downstream in the direction indicated by the arrow in FIG. 7.

In another aspect, the development can also be performed by a method of dipping the sample pad 73 of the nucleic acid detection device in the sample for detection and/or the developing solution in a container (e.g., a PCR tube, an Eppendorf tube, or a 96-well plate) retaining the sample for detection and/or the developing solution. In this case, the width of the sample pad 73 is preferably 2.0 to 10.0 mm, more preferably 2.0 to 5.0 mm, such that the sample pad 73 can be placed in the container retaining the sample for detection and/or the developing solution.

In the nucleic acid detection device that is used by dipping in the container retaining the sample for detection and/or the developing solution, the sample pad 73 can be omitted from the nucleic acid detection device 700 illustrated in FIG. 7. Furthermore, the conjugate pad 72 can also be omitted, if unnecessary, for example, when the labeling agent is used as the labeling part. This nucleic acid detection device can assume a form in which the end part, on the side where the absorption pad 74 is not disposed, of the solid-phase support 71 on the substrate 75 is dipped directly in the sample for detection and/or the developing solution.

In one embodiment wherein the labeling part is the tag for labeling, the nucleic acid for detection comes into contact with a labeling agent upon passing through the conjugate pad 72 retaining the labeling agent so that the nucleic acid for detection is labeled with the labeling agent via the tag for labeling.

Subsequently, the nucleic acid for detection in the sample for detection comes into contact with the capture unit immobilized on the moiety 76 upon passing through the solid-phase support 71 so that the nucleic acid for detection is captured and bound on the solid-phase support 71 via the tag for immobilization.

The labeling agent bound with the nucleic acid for detection captured and bound on the moiety 76 of the solid-phase support 71 comprising the capture unit is detected at the moiety 76 when the nucleic acid for detection is present in the sample for detection. Provided that the labeling agent is visually confirmable, the moiety 76 develops color due to the labeling agent. The presence or absence of the nucleic acid for detection can be identified with the presence or absence of the detection (color development) of the labeling agent as an index. Based on this, the presence or absence of the target nucleic acids in the sample to be analyzed can be identified.

<4. Further Embodiment of Primer Set>

A further embodiment of the primer set of embodiment 1 described above according to one or more embodiments of the present invention does not necessarily have to comprise the labeling part binding to one of the terminal primer A and the terminal primer B and the binding part binding to the other terminal primer.

Specifically, the further embodiment of the primer set according to one or more embodiments of the present invention relates to a primer set comprising:

the terminal primer A;

the kth double-headed primer; and the terminal primer B, wherein

N is an integer of 2 or larger, k is an integer from 1 to N−1, and the kth double-headed primer involves the case where k is 1 to the case where k is N−1.

The nucleic acid amplification reaction using this primer set for a template nucleic acid containing a first target nucleic acid to a Nth target nucleic acid forms a nucleic acid amplification product comprising:

an amplified fragment of the first target nucleic acid;

an amplified fragment in which a moiety of a complementary strand of a kth target nucleic acid and a moiety of a (k+1)th target nucleic acid are linked to each other at their 5' ends; and an amplified fragment of a complementary strand of the Nth target nucleic acid, wherein the first target nucleic acid to the Nth target nucleic acid each hybridize to a complementary strand thereof to form a duplex.

This nucleic acid amplification product can be detected by analyzing a product of the nucleic acid amplification reaction. The detection method may be not only a detection method which involves immobilization on a solid-phase support, but any of other detection methods. For example, a possible method involves detecting the product of the nucleic acid amplification reaction based on a molecular weight or other indices measured by a method such as gel electrophoresis.

EXAMPLES

One or more embodiments of the present invention will be specifically described on the basis of experimental results given below. However, the present invention is not limited by these results.

Example 1

<1. Design of Primer Set for *Salmonella typhimurium* Detection>

A primer set for detecting *Salmonella typhimurium* with the presence of three target nucleic acids as an index was designed as one example of the primer set according to embodiment 1 (the number of target nucleic acids: N=3).

*Salmonella* is classified into one genus, two species, and six subspecies from biochemical properties, DNA homology, etc. Aside from this classification, serotyping has been established on the basis of the combinations of somatic antigens (O antigens) and flagella antigens (H antigens), and 2,500 or more serotypes have been reported so far. 1,500 or more serotypes that cause infection in humans or livestock are classified into subspecies I and are very highly genetically similar to each other. This makes it difficult to determine a serotype through the use of difference in the nucleotide sequence of a single gene.

By contrast, in JP Patent Publication (Kokai) No. 2011-234739 A (2011), the combination of three genes specific for a particular serotype enables identification of the serotypes of *Salmonella typhimurium, Salmonella enteritidis, Salmonella infantis*, and the like. In this method, these three serotype-specific genes are amplified by multiplex PCR and then analyzed by gel electrophoresis, and positivity is determined when all of the three amplification products can be confirmed.

For example, the following primer sets (SEQ ID NOs: 1 to 6) are disclosed for detecting *Salmonella typhimurium*.

TABLE 1

| Serotype | Target region | Primer name | Nucleotide sequence (5'→3') | SEQ ID NO |
| --- | --- | --- | --- | --- |
| Typhimurium | TMP1 | TMP1F | ATGCGGGTATGACAAACCCT | 1 |
|  |  | TMP1R | TTAGCCCCATTTGGACCTTT | 2 |
|  | TMP2 | TMP2F | CAGACCAGGTAAGTTTCTGG | 3 |
|  |  | TMP2R | CGCATATTTGGTGCAGAAAT | 4 |
|  | TMP3 | TMP3F | TTTACCTCAATGGCGGAACC | 5 |
|  |  | TMP3R | CCCAAAAGCTGGGTTAGCAA | 6 |

In this Example, the combination of primers given below was designed, on the basis of SEQ ID NOs: 1 to 6, as the primer set of embodiment 1 for detecting *Salmonella typhimurium* (N=3).

This primer set shown in Table 2 corresponds to an example of the primer set of embodiment 1 (N=3) shown in FIG. 3 wherein the first target nucleic acid 11 is a sense strand of TMP1, the second target nucleic acid 21 is a sense strand of TMP2, and the third target nucleic acid 31 is an antisense strand of TMP3.

TMP1F-Mem of this primer set corresponds to the terminal primer A 100 of FIG. 3. In TMP1F-Mem, the DNA strand (SEQ ID NO: 1) of TMP1F corresponds to the polynucleotide 101, and the tag sequence (SEQ ID NO: 9) underlined in Table 2 corresponds to the terminal primer A added moiety 102. This tag sequence (SEQ ID NO: 9) is a complementary sequence of a solid phase-side tag sequence (SEQ ID NO: 11) immobilized on a membrane serving as a solid-phase support and corresponds to the binding part (tag for immobilization) in the primer set of embodiment 1. In TMP1F-Mem, the tag sequence (SEQ ID NO: 9) and TMP1F (SEQ ID NO: 1) are disposed in the same direction from the 5' end to the 3' end. X shown in Table 2 denotes an azobenzene-modified nucleic acid that stops extension through polymerase reaction and is specifically a divalent group represented by formula I described above.

TMP1R-2F of this primer set corresponds to the first double-headed primer 110 of FIG. 3. In TMP1R-2F, the DNA strand (SEQ ID NO: 2) of TMP1R corresponds to the first polynucleotide 111 of the first double-headed primer, and the DNA strand (SEQ ID NO: 3) of TMP2F corresponds to the second polynucleotide 112 of the first double-headed primer. The DNA strand (SEQ ID NO: 2) of TMP1R and the DNA strand (SEQ ID NO: 3) of TMP2F are disposed in directions opposite to each other and linked through a 5'-5' bond in which the 5' positions of sugars on their respective 5'-terminal nucleotides are bonded to each other via a phosphoric acid group. The DNA strand (SEQ ID NO: 2) of TMP1R and the DNA strand (SEQ ID NO: 3) of TMP2F are bound to each other at their 5'-terminal sides, and their 3' ends are liberated. These primers are capable of extending from their respective 3' ends through DNA polymerase reaction in the presence of a template.

TMP2R-3R of this primer set corresponds to the second double-headed primer 120 of FIG. 3. In TMP2R-3R, the DNA strand (SEQ ID NO: 4) of TMP2R corresponds to the first polynucleotide 121 of the second double-headed primer, and the DNA strand (SEQ ID NO: 6) of TMP3R corresponds to the second polynucleotide 122 of the second double-headed primer. The DNA strand (SEQ ID NO: 4) of TMP2R and the DNA strand (SEQ ID NO: 6) of TMP3R are disposed in directions opposite to each other and linked through a 5'-5' bond in which the 5' positions of sugars on their respective 5'-terminal nucleotides are bonded to each other via a phosphoric acid group. The DNA strand (SEQ ID NO: 4) of TMP2R and the DNA strand (SEQ ID NO: 6) of TMP3R are bound to each other at their 5'-terminal sides, and their 3' ends are liberated. These primers are capable of extending from their respective 3' ends through DNA polymerase reaction in the presence of a template.

TMP3F-Au of this primer set corresponds to the terminal primer B 130 of FIG. 3. In TMP3F-Au, the DNA strand (SEQ ID NO: 5) of TMP3F corresponds to the polynucleotide 131, and the tag sequence (SEQ ID NO: 10) underlined in Table 2 corresponds to the terminal primer B added moiety 132. This tag sequence (SEQ ID NO: 10) is a complementary sequence of a labeling agent-side tag sequence (SEQ ID NO: 12) immobilized on gold colloid serving as a labeling agent and corresponds to the labeling part (tag for labeling) in the primer set of embodiment 1. In TMP3F-Au, the tag sequence (SEQ ID NO: 10) and TMP3F (SEQ ID NO: 5) are disposed in the same direction from the 5' end to the 3' end. X shown in Table 2 denotes an azobenzene-modified nucleic acid that stops extension through polymerase reaction and is specifically a divalent group represented by formula I described above.

The oligonucleotide-bound gold colloid used as a labeling agent was prepared by the following procedures.

Gold Colloid (40 nm, $9.0 \times 10^{10}$ (the number of particles/ml), manufactured by British Biocell International Ltd.) was mixed with a thiol group-containing oligonucleotide represented by SEQ ID NO: 12 given below, and the mixture was incubated at 50° C. for 16 hours. After centrifugation at 6000 rpm for 15 minutes, the supernatant was removed. 0.05 M sodium chloride and a 5 mM phosphate buffer (pH 7) were added to the resultant and mixed therewith, followed by incubation again at 50° C. for 40 hours.

After the incubation, the mixture was centrifuged (6000 rpm, 15 min), and the supernatant was removed. A 5 mM phosphate buffer (pH 7) was added to the resultant. This buffer replacement was performed again.

The prepared gold colloid solution was uniformly added over a glass fiber pad, which was then dried in a vacuum dryer to prepare a conjugate pad.

(Thiol group-containing oligonucleotide):
(SEQ ID NO: 12)
5'-TTGGCTCTGTCTCCGTTGTC-SH-3'

In the thiol group-containing oligonucleotide shown in SEQ ID NO: 12, the 3'-phosphoric acid group of the 3'-terminal cytosine nucleotide and the hydroxy group of a compound represented by HO—$(CH_2)_m$—SH (m is 6) were bonded to each other through a phosphoester bond.

A solid-phase support (membrane) on which a tag capture unit binding to the tag sequence for immobilization (SEQ ID NO: 9) was immobilized was prepared by the following procedures.

A solution containing an oligonucleotide probe represented by SEQ ID NO: 11 given below as the tag capture unit was applied in a line pattern of 1 mm in width orthogonal to the direction of development onto a nitrocellulose membrane manufactured by Merck Millipore (Hi-Flow 180) using a dispenser. Then, the membrane was dried at 40° C. for 30 minutes to prepare a membrane having the tag capture unit.

(Oligonucleotide probe):
(SEQ ID NO: 11)
5'-CACTGGGCATACGGTAGCAT-3'

For detection by nucleic acid chromatography, a lateral flow-type nucleic acid detection device was prepared by the following procedures.

The prepared lateral flow-type nucleic acid detection device was prepared in accordance with the detection device shown in the schematic diagram of FIG. 7.

Specifically, a polypropylene backing sheet (Lohmann Tape Group) as the substrate 75, the conjugate pad retaining the oligonucleotide-bound gold colloid prepared as described above as the conjugate pad 72, the membrane having the oligonucleotide probe (SEQ ID NO: 11) as the tag capture unit prepared as described above as the membrane (solid-phase support) 71 having the moiety 76, a glass fiber sample pad as the sample pad 73, and a cellulose absorption pad as the absorption pad 74 were laminated such that these components overlapped with each other as shown in FIG. 7 to prepare lateral flow-type nucleic acid detection device 700.

| Serotype | Target region | Primer name | Nucleotide sequence (5'→3') | SEQ ID NO |
|---|---|---|---|---|
| Typhimurium | TMP1F-Mem | Terminal primer A (binding pare added) | 5'-ATGCTACCGTATGCCCAGTGX ATGCGGGTATGACAAACCCT-3' | 7 |
| | TMP1R-2F | First double-headed primer | 3'-GGTCTTTGAATGGACCAGAC-5' 5'-TTAGCCCCATTTGGACCTTT-3' | 2 + 3 |
| | TMP2R-3R | Second double-headed primer | 3'-AACGATTGGGTCGAAAACCC-5' 5'-CGCATATTTGGTGCAGAAAT-3' | 4 + 6 |
| | TMP3F-Au | Terminal primer B (labeling part added) | 5'-GACAACGGAGACAGAGCCAAX TTTACCTCAATGGCGGAACC-3' | 8 |

<2. Nucleic Acid Amplification by PCR>

PCR reaction solutions of test plots 1 to 6 were prepared in accordance with Table 3 given below using the primers shown in Table 2 as a primer set and genomic DNA of *Salmonella typhimurium* as a template.

TABLE 3

| Component | 1 | 2 | 3 | 4 | 5 | 6 |
|---|---|---|---|---|---|---|
| 10 μM TMP 1F-Mem solution | 0.5 | 0 | 0 | 0.5 | 0 | 0.5 |
| 10 μM TMP 1R-2F solution | 0.5 | 0.5 | 0 | 0.5 | 0.5 | 0.5 |
| 10 μM TMP 2R-3R solution | 0 | 0.5 | 0.5 | 0.5 | 0.5 | 0.5 |
| 10 μM TMP 3F-Au solution | 0 | 0 | 0.5 | 0 | 0.5 | 0.5 |
| Mixed solution of 2.5 mM each of dNTPs | 1.6 | 1.6 | 1.6 | 1.6 | 1.6 | 1.6 |
| 10 × Taq buffer (supplemented with 20 mM $Mg^{2+}$) | 2 | 2 | 2 | 2 | 2 | 2 |
| 5 U/μl Takara TaqHS | 0.2 | 0.2 | 0.2 | 0.2 | 0.2 | 0.2 |
| *S. Typhimurium* genomic DNA (1 ng/μl) | 0.5 | 0.5 | 0.5 | 0.5 | 0.5 | 0.5 |
| Sterile distilled water | 14.7 | 14.7 | 14.7 | 14.2 | 14.2 | 13.7 |

(unit in the table: μl)

The PCR reaction solution of each test plot described above was loaded in a thermal cycler (Bioer Technology Co., Ltd., LifeEco) and reacted at 95° C. for 2 minutes, followed by 30 cycles each involving 98° C. for 10 seconds, 60° C. for 30 seconds, and 72° C. for 30 seconds.

The PCR product was confirmed by gel electrophoresis and nucleic acid chromatography.

The analysis by gel electrophoresis was conducted by separating 5 μl of the reaction solution on a 2% agarose gel, then staining the gel with ethidium bromide, and detecting a band.

The analysis by nucleic acid chromatography was conducted by adding 5 μl of the reaction solution to the sample pad 73 of the lateral flow-type nucleic acid detection device 700 having the structure shown in FIG. 7, prepared by the procedures described above, then adding 60 μl of a developing buffer to the sample pad 73 for development, and 5 minutes later, confirming line coloring at the moiety 76 of the membrane 71.

<3. Results>

Figure 8:
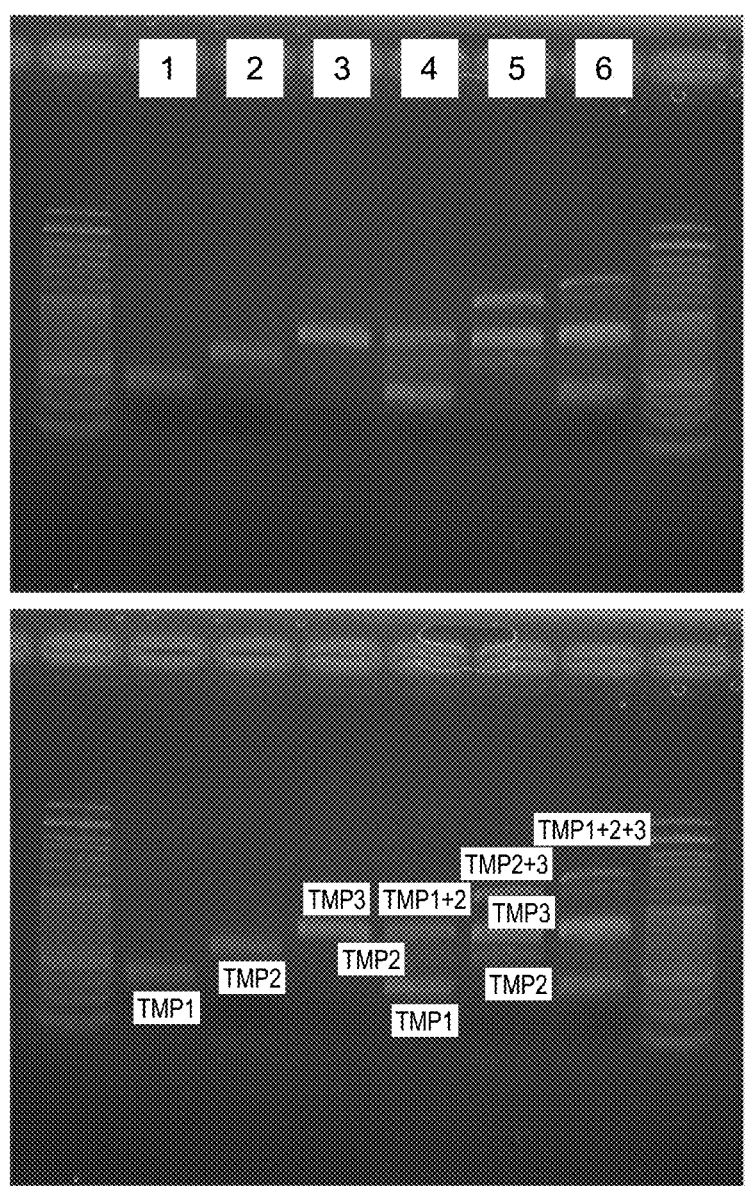
FIG. 8 shows results of gel electrophoresis of an amplification product in Example 1.

The results of gel electrophoresis are shown in FIG. 8. An amplification product of target nucleic acids 1 to 3 linked to each other was confirmed under the conditions using the whole primer set of embodiment 1 (test plot 6). In the test plot 6, an amplification product of one of the target nucleic acids 1 to 3 and an amplification product of two of these target nucleic acids linked to each other were also confirmed in addition to the amplification product of target nucleic acids 1 to 3 linked to each other. The formation of amplification products according to the combinations of the primers was confirmed in the test plots 1 to 5.

Figure 9:
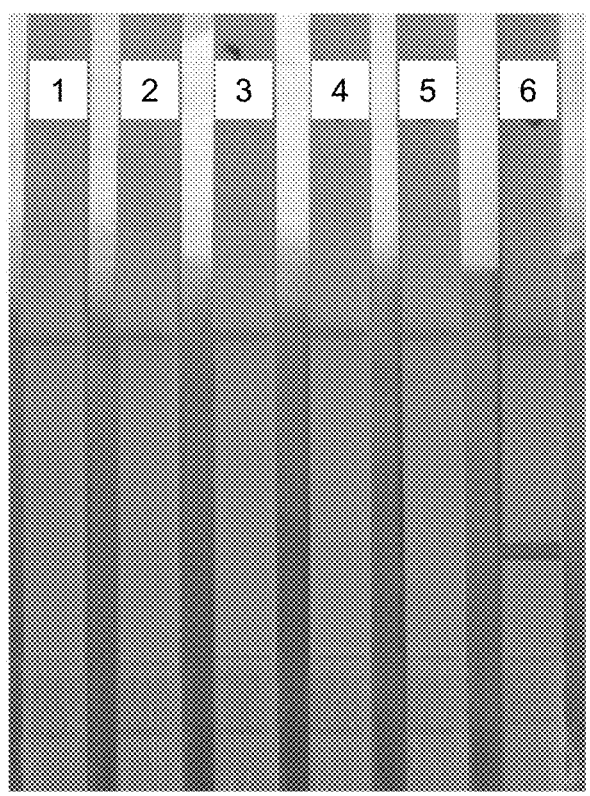
FIG. 9 shows results of nucleic acid chromatography of the amplification product in Example 1.

The results of subjecting each of the PCR reaction solutions of test plots 1 to 6 to nucleic acid chromatography using the lateral flow-type nucleic acid detection device 700 are shown in FIG. 9. Only the test plot 6 in which three amplification products were linked to each other exhibited line coloring.

These results demonstrated that the nucleic acid amplification product 1 shown in FIG. 3C was produced in the PCR reaction solution obtained in the test plot 6 using the genomic DNA of *Salmonella typhimurium* having all the target nucleic acids 1 to 3 as a template and the primer set of embodiment 1.

<4. Confirmation of Specificity>

In order to evaluate the specificity of the method for identifying *Salmonella typhimurium* using the primer set of embodiment 1 consisting of TMP1F-Mem, TMP1R-2F, TMP2R-3R and TMP3F-Au, detection evaluation was conducted using a plurality of bacteria of the genus *Salmonella*. The evaluation was conducted under the conditions of the test plot 6 described above except that genomic DNAs extracted from a plurality of bacteria of the genus *Salmonella* were used as a template.

Figure 10:
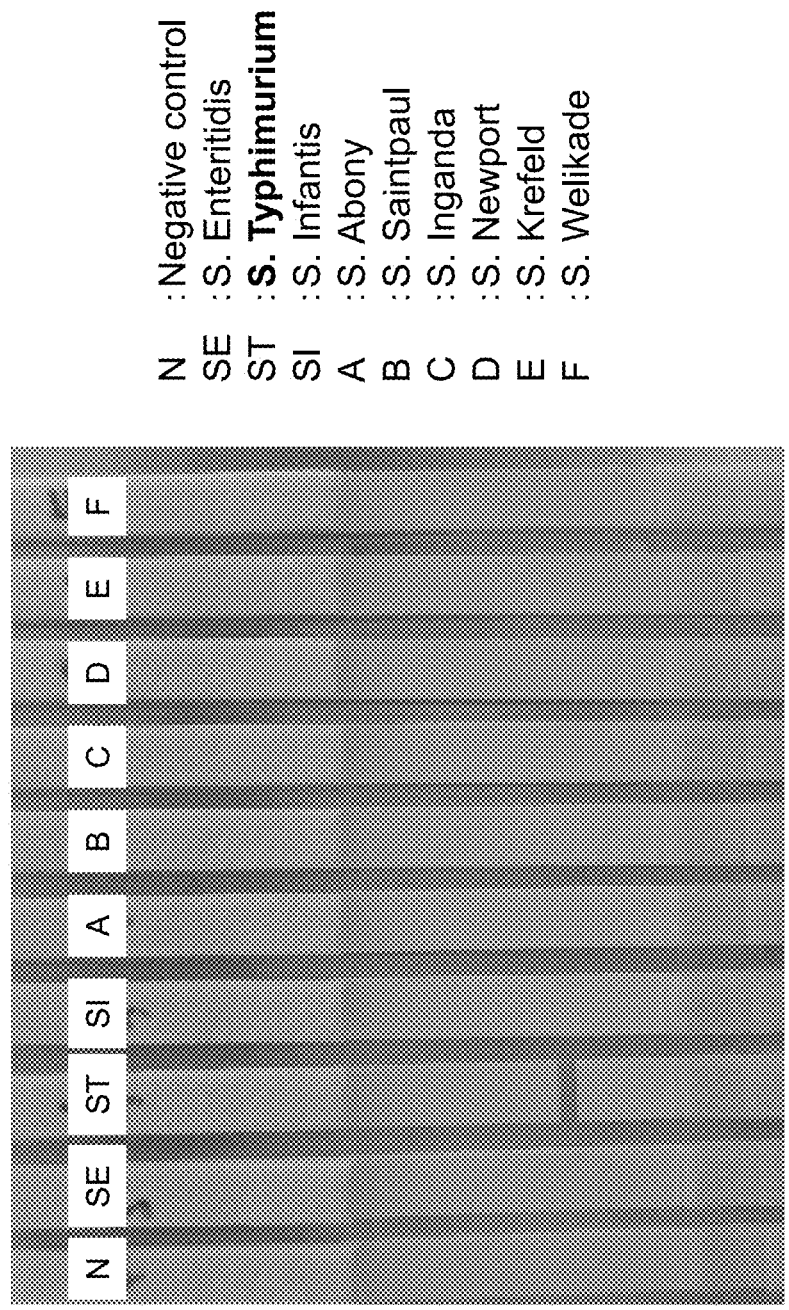
FIG. 10 shows results of nucleic acid chromatography of the amplification product in Example 1.

The results of nucleic acid chromatography using the lateral flow-type nucleic acid detection device 700 are shown in FIG. 10. This method using the primer set of embodiment 1 and nucleic acid chromatography exhibited line coloring only when *Salmonella typhimurium* was used as a template, and was thus found to have sufficient specificity.

The nucleic acid chromatography has the advantages that: the operation is convenient because detection is achieved by merely adding a PCR reaction solution and a developing buffer onto a chip; gel preparation and treatment with a hazardous reagent such as ethidium bromide are unnecessary; etc. Furthermore, the detection time is approximately 5 minutes compared with approximately 60 minutes for gel electrophoresis and thus enables reduction in testing time.

Comparative Example

In Comparative Example, the same operation as in the preceding section 4 was performed except that the primers of SEQ ID NOs: 1 to 6 were used.

After PCR reaction, gel electrophoresis was performed, and band patterns were analyzed.

Figure 11:
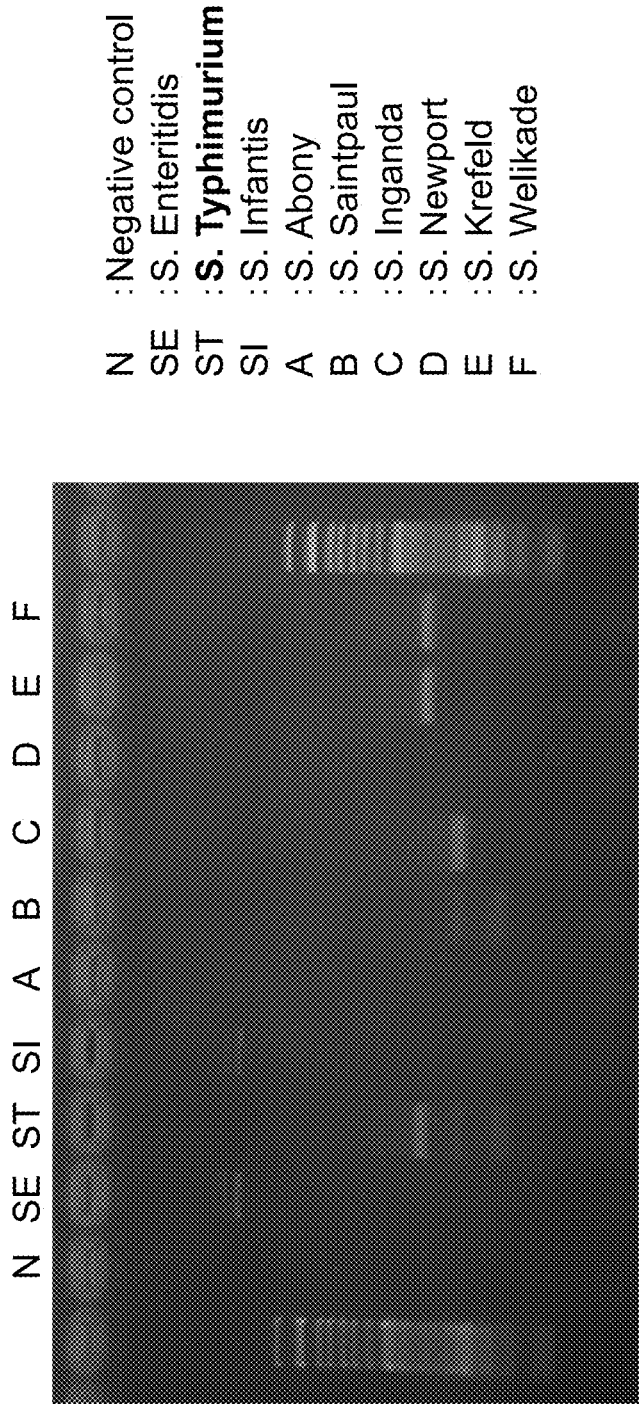
FIG. 11 shows results of gel electrophoresis of an amplification product of a conventional method of individually amplifying three target nucleic acids.

The results are shown in FIG. 11. Three types of bands were detected only when genomic DNA of *Salmonella typhimurium* was used as a template. Thus, this approach achieved specific detection.

The detection of a tandem amplification product using the primer set of embodiment 1 and nucleic acid chromatography exhibited line coloring only in the case of *Salmonella typhimurium* as shown in FIG. 10. By contrast, in the analysis by gel electrophoresis shown in FIG. 11, 1 or 2 bands were detected in some samples, suggesting that the analysis may be difficult.

Example 2

PCR was performed using the primer set according to embodiment 2 and a nucleic acid sample containing two target DNAs as a template. An amplification product contained in the PCR reaction solution was confirmed by nucleic acid chromatography and gel electrophoresis.

A region having 208 bases and a region having 131 bases, contained in DNA of a pathogenic microbe were used as a first target region and a second target region, respectively. One of the DNA strands of each target region was used as a target nucleic acid.

Hereinafter, this example will be described with reference to the reference numerals shown in FIG. 4.

The terminal primer A 200 used was DNA consisting of nucleotide sequence 201 identical to a 5'-terminal region of 24 bases of the first target nucleic acid, and a tag sequence for labeling (SEQ ID NO: 10) bound at its 3' end to the 5'-terminal side of the nucleotide sequence 201 via a divalent group represented by formula I described above. The tag sequence for labeling (SEQ ID NO: 10) is a complementary sequence of a labeling agent-side tag sequence (SEQ ID NO: 12) immobilized on gold colloid serving as a labeling agent.

The first reverse primer 210 used was DNA comprising nucleotide sequence 211 identical to a 5'-terminal region of 25 bases of a complementary strand of the first target nucleic acid, and nucleotide sequence $B_1$ 212 of 20 bases bound at its 3' end to the 5'-terminal side of the nucleotide sequence 211.

The second forward primer 220 used was DNA comprising nucleotide sequence 221 identical to a 5'-terminal region of 20 bases of the second target nucleic acid, and nucleotide sequence $D_2$ 222 of 20 bases bound at its 3' end to the 5'-terminal side of the nucleotide sequence 221. The nucleotide sequence $B_1$ 212 and the nucleotide sequence $D_2$ 222 are sequences complementary to each other.

The terminal primer B 230 used consisted of nucleotide sequence 231 identical to a 5'-terminal region of 20 bases of a complementary strand of the second target nucleic acid, and a tag sequence for immobilization (SEQ ID NO: 9) bound at its 3' end to the 5'-terminal side of the nucleotide sequence 231 via a divalent group represented by formula I described above. The tag sequence for immobilization (SEQ ID NO: 9) is a complementary sequence of a solid phase-side tag sequence (SEQ ID NO: 11) immobilized on a membrane serving as a solid-phase support.

A test plot using a template DNA containing the first target region but no second target region (template 1), a test plot using a template DNA containing the second target region but no first target region (template 2), a test plot using a template DNA containing the first target region and the second target region (template 1+2), and a test plot containing no template DNA (N) were provided.

The same PCR reaction solution as in Table 2 was prepared except that: in the PCR reaction solution shown in Table 2 described above, the terminal primer A 200, the first reverse primer 210, the second forward primer 220, and the terminal primer B 230 described above were used as primer components; template DNA according to each test plot described above was used as template DNA; and the final volume was adjusted to 20.0 μL with sterile distilled water.

A PCR reaction solution having a terminal primer A 200: first reverse primer 210: second forward primer 220: terminal primer B 230 molar ratio of 1:1:1:1 and a PCR reaction solution having a terminal primer A 200: first reverse primer 210: second forward primer 220: terminal primer B 230 molar ratio of 1:0.1:0.1:1 were prepared for each test plot.

PCR, nucleic acid chromatography, and gel electrophoresis were performed under the same conditions as in Example 1.

Figure 12:
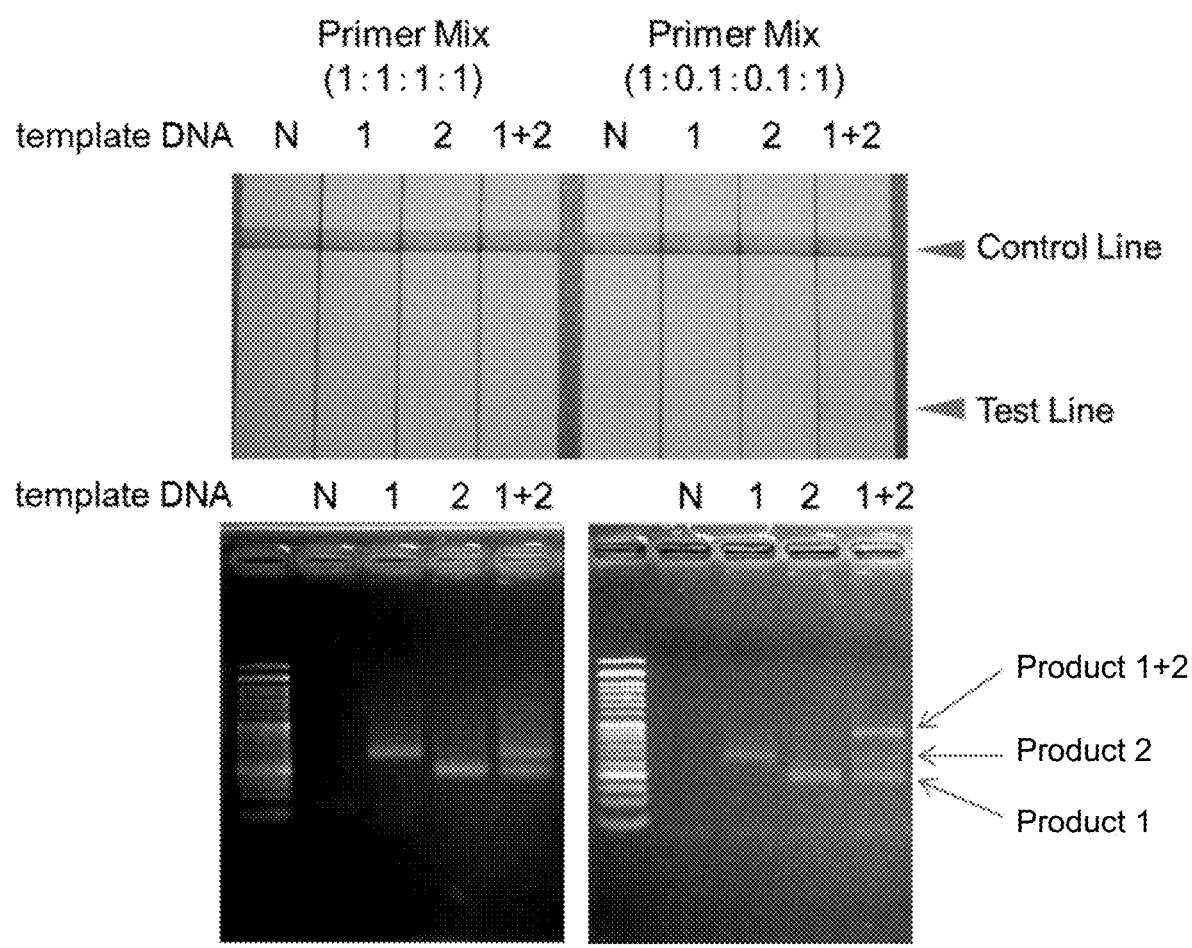
FIG. 12 shows results of nucleic acid chromatography of an amplification product in Example 2 (upper diagram) and results of gel electrophoresis of the amplification product in Example 2 (lower diagram).

The results of nucleic acid chromatography are shown in the upper diagram of FIG. 12, and the results of gel electrophoresis are shown in the lower diagram of FIG. 12.

In the case of using the PCR reaction solution having a terminal primer A 200: first reverse primer 210: second forward primer 220: terminal primer B 230 molar ratio of 1:0.1:0.1:1 in the template 1+2 test plot, an amplification product of the first target nucleic acid and the second target nucleic acid linked to each other was formed in a sufficient amount and was detected as one colored band in nucleic acid chromatography.

The primer set, the method and the kit according to one or more embodiments of the present invention are useful in the detection of nucleic acids.

All publications, patents and patent applications cited herein are incorporated herein by reference in their entirety.

Although the disclosure has been described with respect to only a limited number of embodiments, those skilled in the art, having the benefit of this disclosure, will appreciate that various other embodiments may be devised without departing from the scope of the present invention. Accordingly, the scope of the invention should be limited only by the attached claims.

SEQUENCE LISTING

The instant application contains a Sequence Listing entitled "SEQUENCELISTING.TXT" (2,170,756 bytes) and created on Dec. 11, 2018, which is submitted electronically via EFS-Web in ASCII format herewith and is hereby incorporated by reference in its entirety. The Sequence Listing, filed in accordance with 37 CFR § 1.821(g), does not include new matter.

What is claimed is:

1. A primer set for preparing a nucleic acid amplification product detectable on a solid-phase support, the primer set comprising:
   a terminal primer A comprising, in a 3'-terminal part of the terminal primer A, a nucleotide sequence that hybridizes to a 3'-terminal part of a complementary sequence of a first target nucleic acid;
   a k-th double-headed primer comprising two polynucleotides linked at 5' terminal sides of the two polynucleotides, wherein one of the two polynucleotides comprises, in a 3'-terminal part of the one of the two polynucleotides, a nucleotide sequence that hybridizes to a 3'-terminal part of a nucleotide sequence of a k-th target nucleic acid, and the other polynucleotide comprises, in a 3'-terminal part of the other polynucleotide, a nucleotide sequence that hybridizes to a 3'-terminal part of a complementary sequence of a (k+1)th target nucleic acid; and
   a terminal primer B comprising, in a 3'-terminal part of the terminal primer B, a nucleotide sequence that hybridizes to a 3'-terminal part of a nucleotide sequence of a N-th target nucleic acid,
   wherein N is an integer of 2 or larger, and k is an integer from 1 to N−1, and
   wherein one of the terminal primer A and the terminal primer B further comprises a labeling part which is a labeling agent or is a tag capable of binding to a labeling agent, and the other terminal primer further comprises a binding part which is a tag capable of binding to the solid-phase support.

2. The primer set according to claim 1, wherein the binding part is a tag comprising a polynucleotide capable of binding to the solid-phase support.

3. A method for detecting two or more target nucleic acids, the method comprising:
   preparing a sample for detection by performing a nucleic acid amplification reaction using the primer set according to claim 1 and a template nucleic acid obtained from a sample to be analyzed,
   contacting the sample for detection with a solid-phase support comprising a moiety capable of binding to the binding part; and
   detecting a nucleic acid for detection at the moiety of the solid-phase support with the labeling part as an index.

4. The method according to claim 3,
   wherein the nucleic acid amplification reaction is performed using two or more primer sets,
   wherein the two or more primer sets are designed so as to be able to produce two or more of the nucleic acids for detection each comprising a different combination of the two or more target nucleic acids and each having the binding part capable of binding to a distinct position of the solid-phase support, and wherein detecting the nucleic acid for detection comprises contacting the sample for detection with the solid-phase support, and detecting each of the two or more nucleic acids for detection on the solid-phase support with the labeling part as an index.

5. A kit for detecting two or more target nucleic acids in a sample to be analyzed, the kit comprising:
   a primer set according to claim 1; and
   a solid-phase support comprising a moiety capable of binding to the binding part.

6. The kit according to claim 5, comprising a nucleic acid detection device, wherein the nucleic acid detection device comprises the solid-phase support and a reaction system reception part for receiving a product of a nucleic acid amplification reaction.

7. The kit according to claim 5,
   wherein the labeling part is the tag capable of binding to the labeling agent, and
   wherein the kit further comprises a labeling agent capable of binding to the tag as the labeling part.

8. The kit according to claim 7, comprising a nucleic acid detection device, wherein the nucleic acid detection device comprises the labeling agent, the solid-phase support, a labeling agent retention part which retains the labeling agent, and a reaction system reception part for receiving a product of nucleic acid amplification reaction.

9. A primer set for preparing a nucleic acid amplification product, the primer set comprising:
   a terminal primer A comprising, in a 3'-terminal part of the terminal primer A, a nucleotide sequence that hybridizes to a 3'-terminal part of a complementary sequence of a first target nucleic acid;
   a k-th double-headed primer comprising two polynucleotides linked at 5' terminal sides of the two polynucleotides, wherein one of the two polynucleotides comprises, in a 3'-terminal part of the one of the two polynucleotides, a nucleotide sequence that hybridizes to a 3'-terminal part of a nucleotide sequence of a k-th target nucleic acid, and the other polynucleotide comprises, in a 3'-terminal part of the other polynucleotide, a nucleotide sequence that hybridizes to a 3'-terminal part of a complementary sequence of a (k+1)th target nucleic acid; and
   a terminal primer B comprising, in a 3'-terminal part of the terminal primer B, a nucleotide sequence that hybridizes to a 3'-terminal part of a nucleotide sequence of a N-th target nucleic acid,
   wherein N is an integer of 2 or larger, and k is an integer from 1 to N−1.

10. A method for detecting two or more target nucleic acids, the method comprising:
    performing a nucleic acid amplification reaction using a nucleic acid obtained from a sample to be analyzed as a template, and the primer set according to claim 9; and
    detecting a nucleic acid amplification product in a product of the nucleic acid amplification reaction.

* * * * *